(12) United States Patent
LeBoeuf et al.

(10) Patent No.: US 9,788,794 B2
(45) Date of Patent: Oct. 17, 2017

(54) METHOD AND APPARATUS FOR GENERATING ASSESSMENTS USING PHYSICAL ACTIVITY AND BIOMETRIC PARAMETERS

(71) Applicant: Valencell, Inc., Raleigh, NC (US)

(72) Inventors: Steven F. LeBoeuf, Raleigh, NC (US); Michael Edward Aumer, Raleigh, NC (US); Eric Douglas Romesburg, Chapel Hill, NC (US)

(73) Assignee: VALENCELL, INC., Raleigh, NC (US)

( * ) Notice: Subject to any disclaimer, the term of this patent is extended or adjusted under 35 U.S.C. 154(b) by 0 days.

(21) Appl. No.: 15/120,766

(22) PCT Filed: Feb. 27, 2015

(86) PCT No.: PCT/US2015/018049
§ 371 (c)(1),
(2) Date: Aug. 23, 2016

(87) PCT Pub. No.: WO2015/131065
PCT Pub. Date: Sep. 3, 2015

(65) Prior Publication Data
US 2016/0361020 A1 Dec. 15, 2016

Related U.S. Application Data

(60) Provisional application No. 61/945,960, filed on Feb. 28, 2014.

(51) Int. Cl.
*A61B 5/00* (2006.01)
*A61B 5/11* (2006.01)
(Continued)

(52) U.S. Cl.
CPC .............. *A61B 5/721* (2013.01); *A61B 5/026* (2013.01); *A61B 5/02055* (2013.01);
(Continued)

(58) Field of Classification Search
CPC .. G01L 9/12; G01L 9/04; A61B 5/026; A61B 5/721
(Continued)

(56) References Cited

U.S. PATENT DOCUMENTS 3,636,617 A   1/1972   Schmidt et al.
3,704,706 A   12/1972  Herczfeld et al.
(Continued)

FOREIGN PATENT DOCUMENTS

WO      0021435 A1   4/2000
WO   2007013054 A1   2/2007
(Continued)

OTHER PUBLICATIONS

Zhu, Hongsheng, et al., "Walking Cadence Effect on Plantar Pressures," Archives of Physical Medicine and Rehabilitation, vol. 76, No. 11, Nov. 1, 1995, XP004647708, pp. 1000-1005. ISSN: 0003-9993.

(Continued)

*Primary Examiner* — Jewel V Thompson
(74) *Attorney, Agent, or Firm* — Coats & Bennett, PLLC

(57) ABSTRACT

The methods and apparatuses presented herein determine and/or improve the quality of one or more physiological assessment parameters, e.g., response-recovery rate, based on biometric signal(s) and/or motion signal(s) respectively output by one or more biometric and/or motion sensors. The disclosed methods and apparatuses also estimate a user's stride length based on a motion signal and a determined type (Continued)

US 9,788,794 B2

Page 2 of user motion, e.g., walking or running. The speed of the user may then be estimated based on the estimated stride length.

9 Claims, 18 Drawing Sheets

(51) Int. Cl.
G06F 19/00 (2011.01)
A61B 5/0205 (2006.01)
A61B 5/026 (2006.01)
A61B 5/021 (2006.01)
A61B 5/024 (2006.01)
A61B 5/0456 (2006.01)
A61B 5/08 (2006.01)
A61B 5/091 (2006.01)

(52) U.S. Cl.
CPC ........ A61B 5/02438 (2013.01); A61B 5/1118 (2013.01); A61B 5/1123 (2013.01); A61B 5/6815 (2013.01); A61B 5/7235 (2013.01); A61B 5/7239 (2013.01); A61B 5/7242 (2013.01); G06F 19/3406 (2013.01); G06F 19/3481 (2013.01); A61B 5/021 (2013.01); A61B 5/02108 (2013.01); A61B 5/02405 (2013.01); A61B 5/02416 (2013.01); A61B 5/0456 (2013.01); A61B 5/0816 (2013.01); A61B 5/091 (2013.01); A61B 5/7203 (2013.01); A61B 2562/0219 (2013.01)

(58) Field of Classification Search
USPC .................................................. 73/718, 726
See application file for complete search history.

(56) References Cited

U.S. PATENT DOCUMENTS

| | | | |
|---|---|---|---|
| 4,672,976 A | | 6/1987 | Kroll |
| 4,769,738 A * | | 9/1988 | Nakamura ............ G01L 9/0073 361/283.1 |
| 4,952,928 A | | 8/1990 | Carroll et al. |
| 4,955,379 A | | 9/1990 | Hall |
| 5,139,025 A | | 8/1992 | Lewis et al. |
| 5,243,992 A | | 9/1993 | Eckerle et al. |
| 5,263,491 A | | 11/1993 | Thornton |
| 5,297,548 A | | 3/1994 | Pologe |
| 5,299,570 A | | 4/1994 | Hatschek |
| 5,448,082 A | | 9/1995 | Kim |
| 5,482,036 A | | 1/1996 | Diab et al. |
| 5,494,043 A | | 2/1996 | O'sullivan et al. |
| 5,503,016 A | | 4/1996 | Koen |
| 5,575,284 A | | 11/1996 | Athan et al. |
| 5,673,692 A | | 10/1997 | Schulze et al. |
| 5,807,267 A | | 9/1998 | Bryars et al. |
| 5,846,190 A | | 12/1998 | Woehrle |
| 5,853,005 A | | 12/1998 | Scanlon |
| 5,906,582 A | | 5/1999 | Kondo et al. |
| 5,954,644 A | | 9/1999 | Dettling et al. |
| 5,964,701 A | | 10/1999 | Asada et al. |
| 6,022,748 A | | 2/2000 | Charych et al. |
| 6,135,951 A | | 10/2000 | Richardson et al. |
| 6,198,394 B1 | | 3/2001 | Jacobsen et al. |
| 6,267,721 B1 | | 7/2001 | Welles |
| 6,341,527 B1 * | | 1/2002 | Ishikura ................ G01L 9/0075 73/718 |
| 6,393,311 B1 | | 5/2002 | Edgar, Jr. et al. |
| 6,443,890 B1 | | 9/2002 | Schulze et al. |
| 6,491,647 B1 | | 12/2002 | Bridger et al. |
| 6,527,711 B1 | | 3/2003 | Stivoric et al. |
| 6,608,562 B1 | | 8/2003 | Kimura et al. |
| 6,611,789 B1 | | 8/2003 | Darley |
| 6,656,151 B1 | | 12/2003 | Blatter |
| 6,725,072 B2 | | 4/2004 | Steuer et al. |
| 6,748,254 B2 | | 6/2004 | O'Neil et al. |
| 6,948,374 B2 * | | 9/2005 | Miyashita ............ G01L 9/0042 73/718 |
| 6,995,665 B2 | | 2/2006 | Appelt et al. |
| 6,997,879 B1 | | 2/2006 | Turcott |
| 7,336,982 B2 | | 2/2008 | Yoo |
| 7,378,954 B2 | | 5/2008 | Wendt |
| 7,539,533 B2 | | 5/2009 | Tran |
| 7,827,000 B2 * | | 11/2010 | Stirling ................ A61B 5/1038 702/141 |
| 8,230,746 B2 * | | 7/2012 | Miyashita ............ G01L 9/0073 73/718 |
| 8,679,012 B1 * | | 3/2014 | Kayyali ................ A61B 5/0002 382/115 |
| 8,712,723 B1 * | | 4/2014 | Kahn ..................... G01B 21/02 377/24.2 |
| 8,903,671 B2 * | 12/2014 | Park ....................... G08B 21/18 702/104 |
| 8,923,941 B2 | | 12/2014 | LeBoeuf et al. |
| 8,945,017 B2 * | | 2/2015 | Venkatraman ......... A61B 5/721 600/500 |
| 9,044,180 B2 | | 6/2015 | Leboeuf et al. |
| 9,173,576 B2 * | | 11/2015 | Yuen .................... G06F 19/3418 |
| 9,538,921 B2 * | | 1/2017 | LeBoeuf .............. A61B 5/0205 |
| 2002/0013538 A1 | | 1/2002 | Teller |
| 2003/0065269 A1 | | 4/2003 | Vetter et al. |
| 2003/0109791 A1 | | 6/2003 | Kondo et al. |
| 2003/0176815 A1 | | 9/2003 | Baba et al. |
| 2003/0233051 A1 | | 12/2003 | Verjus et al. |
| 2003/0236647 A1 | | 12/2003 | Yoon et al. |
| 2004/0004547 A1 | | 1/2004 | Appelt et al. |
| 2004/0039254 A1 | | 2/2004 | Stivoric et al. |
| 2004/0054291 A1 | | 3/2004 | Schulz et al. |
| 2004/0059236 A1 | | 3/2004 | Margulies et al. |
| 2004/0178913 A1 | | 9/2004 | Penuela et al. |
| 2004/0186387 A1 | | 9/2004 | Kosuda et al. |
| 2004/0242976 A1 | | 12/2004 | Abreu |
| 2004/0254501 A1 | | 12/2004 | Mault |
| 2005/0007582 A1 | | 1/2005 | Villers et al. |
| 2005/0054938 A1 | | 3/2005 | Wehman et al. |
| 2005/0059870 A1 | | 3/2005 | Aceti |
| 2005/0192516 A1 | | 9/2005 | Takiguchi et al. |
| 2005/0209516 A1 | | 9/2005 | Fraden |
| 2005/0228463 A1 | | 10/2005 | Mac et al. |
| 2005/0245839 A1 | | 11/2005 | Stivoric et al. |
| 2006/0063980 A1 | | 3/2006 | Hwang et al. |
| 2006/0064037 A1 | | 3/2006 | Shalon et al. |
| 2006/0074322 A1 | | 4/2006 | Nitzan |
| 2006/0084879 A1 | | 4/2006 | Nazarian et al. |
| 2007/0016086 A1 | | 1/2007 | Inukai et al. |
| 2007/0116314 A1 | | 5/2007 | Grilliot et al. |
| 2007/0135717 A1 | | 6/2007 | Uenishi et al. |
| 2008/0076972 A1 | | 3/2008 | Dorogusker et al. |
| 2008/0081972 A1 | | 4/2008 | Debreczeny |
| 2008/0132798 A1 | | 6/2008 | Hong et al. |
| 2008/0146890 A1 | | 6/2008 | LeBoeuf et al. |
| 2008/0154098 A1 | | 6/2008 | Morris et al. |
| 2008/0177162 A1 | | 7/2008 | Bae et al. |
| 2008/0269625 A1 | | 10/2008 | Halperin et al. |
| 2009/0010461 A1 | | 1/2009 | Klinghult et al. |
| 2009/0097689 A1 | | 4/2009 | Prest et al. |
| 2009/0105556 A1 | | 4/2009 | Fricke et al. |
| 2009/0131761 A1 | | 5/2009 | Moroney, III et al. |
| 2009/0281435 A1 | | 11/2009 | Ahmed et al. |
| 2009/0306736 A1 | | 12/2009 | Dobak, III |
| 2012/0010478 A1 | | 1/2012 | Kinnunen et al. |
| 2012/0229270 A1 | | 9/2012 | Morley et al. |
| 2012/0303319 A1 | | 11/2012 | Kirkeby |
| 2013/0006583 A1 | | 1/2013 | Weast et al. |
| 2013/0131519 A1 | | 5/2013 | LeBoeuf et al. |
| 2014/0031703 A1 | | 1/2014 | Rayner et al. |
| 2014/0035761 A1 | | 2/2014 | Burton et al. |

FOREIGN PATENT DOCUMENTS

| | | |
|---|---|---|
| WO | 2007122375 A2 | 11/2007 |
| WO | 2009021147 A1 | 2/2009 |

(56) References Cited

FOREIGN PATENT DOCUMENTS

| WO | 2011105914 A1 | 9/2011 |
|---|---|---|
| WO | 2011149922 A1 | 12/2011 |
| WO | 2013028581 A1 | 2/2013 |

OTHER PUBLICATIONS

Buchanan, T., et al., "Neuromusculoskeletal Modeling: Estimation of Muscle Forces and Joint Moments and Movements From Measurements of Neural Command," J Appl Biomech, vol. 20, No. 4, Nov. 1, 2004, pp. 1-34.

Stolwijk, J., "Mathematical Models of Thermal Regulation," Annals of the New York Academy of Sciences, vol. 335, No. 1, Jan. 1, 1980, pp. 98-106.

Wiggs, L, et al., "Sleep patterns and sleep disorders in children with autistic spectrum disorders: insights using parent report and actigraphy," Developmental Medicine and Child Neurology 2004, vol. 46, No. 6, Jan. 1, 2004, pp. 372-380.

Hastings, P.C., "Symptom burden of sleep-disordered breathing in mild-to-moderate congestive heart failure patients," European Respiratory Journal, vol. 27, No. 4, Jan. 1, 2006, pp. 748-755.

Carskadon, M., et al., "Chapter 2—Normal Human Sleep: an Overview," Monitoring and staging human sleep, from Principles and practice of sleep medicine, 5th edition, St. Louis: Elsevier Saunders, Jan. 1, 2011, pp. 1-21.

Critchley, H, "Electrodermal Responses: What Happens in the Brain," The Neuroscientist, vol. 8, No. 2, Jan. 1, 2002, pp. 132-142.

Lang, P., et al., "Looking at pictures: Affective, facial, visceral, and behavioral reactions," Psychophysiology, vol. 30, No. 3, Apr. 22, 1992, pp. 261-273.

Soleymani, M., et al., "Affective Ranking of Movie Scenes Using Physiological Signals and Content Analysis," Proc. 2nd ACM Work. Multimed. Semant., Jan. 1, 2008, pp. 1-8.

Appelhans, B., et al., "Heart Rate Variability as an Index of Regulated Emotional Responding," Review of General Psychology, vol. 10, No. 3, Sep. 15, 2005, pp. 229-240.

Postma, D.S., et al., "The natural history of chronic obstructive pulmonary disease," European Respiratory Monograph, vol. 38, Jan. 1, 2006, pp. 71-83.

Bidargaddi, N., et al., "Ambulatory monitor derived clinical measures for continuous assessment of cardiac rehabilitation patients in a community care model," Pervasive Computing Technologies for Healthcare, 2008 Second International Conference on Pervasive Computing Technologies for Healthcare, Jan. 30, 2008, pp. 1-5.

Hertzman, A., "The Blood Supply of Various Areas as Estimated by the Photoelectric Plethysmograph," Am J. Physiol, vol. 124, Issue 2, Jul. 18, 1938, pp. 328-340.

Hayes, M., et al., "Artifact reduction in photoplethysmography," Applied Optics, vol. 37, No. 31, Nov. 1, 1998, pp. 7437-7446.

Page, E., et al., "Physiological approach to monitor patients in congestive heart failure: application of a new implantable device-based system to monitor daily life activity and ventilation," Europace, vol. 9, May 3, 2007, pp. 687-693.

Moy, M., et al., "Free-living physical activity in COPD: Assessment with accelerometer and activity checklist," Journal of Rehabilitation Research & Development, vol. 46, No. 2, Nov. 2, 2009, pp. 277-286.

Bennett, T., et al., "Development of Implantable Devices for Continuous Ambulatory Monitoring of Central Hemodynamic Values in Heart Failure Patients," Pacing Clin Electrophysiol. Jun. 2005; vol. 28, No. 6, Jun. 1, 2005, pp. 573-584.

Allen, J., "Photoplethysmography and its application in clinical physiological measurement," Physiological Measurement, vol. 28, Feb. 20, 2007, pp. 1-39.

Webster, J.G. (ed.), "Design of Pulse Oximeters," Institute of Physics Publishing, Philadelphia, PA, Jan. 1, 1997, pp. 1-134.

Webster, J.G. (ed.), "Design of Pulse Oximeters," Institute of Physics Publishing, Philadelphia, PA, Jan. 1, 1997, pp. 135-267.

Shevchenko, Y, et al., "90th Anniversary of the Development by Nikolai S. Korotkoff of the Ascultatory Method of Measuring Blood Pressure," Circulation, vol. 94, No. 2, Jul. 15, 1996, pp. 116-118.

Han, H., et al., "Development of a wearable monitoring device with motion artifact reduced algorithm," International Conference on Control, Automation and Systems 2007, Oct. 17, 2007, Seoul, Korea, pp. 1581-1584.

Petition for Inter Partes Review of U.S. Pat. No. 8,157,730; *Apple, Inc.* (Petitioner) v. *Valencell, Inc.* (Patent Owner), IPR 2017-01701, filed Jun. 30, 2017, pp. 1-89.

Petition for Inter Partes Review of U.S. Pat. No. 8,652,040; *Apple, Inc.* (Petitioner) v. *Valencell, Inc.* (Patent Owner), IPR 2017-01702, filed Jun. 30, 2017, pp. 1-70.

Petition for Inter Partes Review of U.S. Pat. No. 8,652,040; *Apple, Inc.* (Petitioner) v. *Valencell, Inc.* (Patent Owner), IPR 2017-01703, filed Jun. 30, 2017, pp. 1-79.

Petition for Inter Partes Review of U.S. Pat. No. 8,888,701; *Apple, Inc.* (Petitioner) v. *Valencell, Inc.* (Patent Owner), IPR 2017-01704, filed Jun. 30, 2017, pp. 1-84.

Declaration of Dr. Majid Sarrafzadeh, Exhibit 1003, Petition for Inter Partes Review of U.S. Pat. No. 8,888,701; *Apple, Inc.* (Petitioner) v. *Valencell, Inc.* (Patent Owner), IPR 2017-01704, filed Jun. 30, 2017, pp. 1-109.

Declaration of Brian W. Anthony, Ph.D. In Support of Petition for Inter Partes Review of U.S. Pat. No. 8,157,730, Exhibit 1003, Petition for Inter Partes Review of U.S. Pat. No. 8,157,730; *Apple, Inc.* (Petitioner) v. *Valencell, Inc.* (Patent Owner), IPR 2017-01701, filed Jun. 30, 2017, pp. 1-138.

Declaration of Dr. Majid Sarrafzadeh, Exhibit 1003, Petition for Inter Partes Review of U.S. Pat. No. 8,652,040; *Apple, Inc.* (Petitioner) v. *Valencell, Inc.* (Patent Owner), IPR 2017-01703, filed Jun. 30, 2017, pp. 1-87.

Declaration of Dr. Majid Sarrafzadeh, Exhibit 1003, Petition for Inter Partes Review of U.S. Pat. No. 8,652,040; *Apple, Inc.* (Petitioner) v. *Valencell, Inc.* (Patent Owner), IPR 2017-01702, filed Jun. 30, 2017, pp. 1-92.

Asada, H., et al., "Mobile Monitoring with Wearable Photoplethysmographic Biosensors," IEEE Engineering in Medicine and Biology Magazine, May/Jun. 2003 Issue, May 1, 2003, pp. 28-40.

Wang, L. et al. "Multichannel Reflective PPG Earpiece Sensor with Passive Motion Cancellation," IEEE Transactions on Biomedical Circuits and Systems, vol. 1, No. 4, Dec. 1, 2007, pp. 235-241.

Wise, K., "Integrated sensors, MEMS, and microsystems: Reflections on a fantastic voyage," Sensors and Actuators A, vol. 136, Feb. 5, 2007, pp. 39-50.

Gigoi, B.P., et al., "Integration Technology for MEMS Automotive Sensors," 28th Annual Conference of the IEEE, Jan. 1, 2002, pp. 2712-2717.

Ko, W., "Trends and frontiers of MEMS," Sensors and Actuators A, vol. 136, Feb. 1, 2007, pp. 62-67.

Barbour, N., "Inertial Sensor Technology Trends," IEEE Sensors Journal, vol. 1, No. 4, Dec. 1, 2001, pp. 332-339.

Vigario, R., "Independent Component Approach to the Analysis of EEG and MEG Recordings," IEEE Transactions on Biomedical Engineering, vol. 47, No. 5, May 1, 2000, pp. 589-593.

Mayer-Kress, G., "Localized Measures for Nonstationary Time-Series of Physiological Data," Integr. Physiol. Behav. Sci., vol. 29, No. 3, Jul. 1, 1994, pp. 205-210.

Shaw, G.A., et al., "Warfighter Physiological and Environmental Monitoring: A Study for the U.S. Army Research Institute in Environmental Medicine and the Soldier Systems Center," Lincoln Laboratory, Massachusetts Institute of Technology, Lexington, MA., Nov. 1, 2004, pp. 1-128.

Laguna, P., et al., "Power Spectral Density of Unevenly Sampled Data by Least-Square Analysis: Performance and Application to Heart Rate Signals," IEEE Transactions on Biomedical Engineering, vol. 45, No. 6, Jun. 1, 1998, pp. 698-715.

Richardson, J.E., "Physiological Responses of Firefighters Wearing Level 3 Chemical Protective Suits While Working in Controlled Hot Environments," J. Occup. Environ. Med., vol. 43, No. 12, Dec. 1, 2001, pp. 1064-1072.

(56) References Cited

OTHER PUBLICATIONS

Scanlon, M., "Acoustic Sensors in the Helmet Detect Voice and Physiology," Proceedings of SPIE, vol. 5071, Jan. 1, 2003, pp. 41-51.

Arnold, M., et al., "Adaptive AR Modeling of Nonstationary Time Series by Means of Kalman Filtering," IEEE Transactions on Biomedical Engineering, vol. 45, No. 5, May 1, 1998, pp. 553-562.

Yan, Y., et al., "Reduction of motion artifact in pulse oximetry by smoothed pseudo Wigner-Ville distribution," Journal of NeuroEngineering and Rehabilitation, vol. 2, No. 3, Mar. 1, 2005, pp. 1-9.

Lee, C.M., et al., "Reduction of Motion Artifacts from Photoplethysmographic Recordings Using a Wavelet Denoising Approach," IEEE EMBS Asian-Pacific Conference on Biomedical Engineering, Jan. 1, 2003, pp. 194-195.

Foo, J.Y.A., "Comparison of wavelet transformation and adaptive filtering in restoring artefact-induced time-related measurement," Biomedical Signal Processing and Control vol. 1, No. 1 (2006), Mar. 24, 2006, pp. 93-98.

Wood, L., et al., "Active Motion Artifact Reduction for Wearable Sensors Using Laguerre Expansion and Signal Separation," Proceedings of the 2005 IEEE Engineering in Medicine and Biology 27th Annual Conference, Shanghai, China, Sep. 1, 2005, pp. 3571-3574.

Cacioppo, J., "Inferring Psychological Significance From Physiological Signals," American Psychologist, vol. 45, No. 1, American Psychological Association, Jan. 1, 1990, pp. 16-28.

Rhee, S., et al., "Artifact-Resistant Power-Efficient Design of Finger-Ring Plethysmographic Sensors," IEEE Transactions on Biomedical Engineering, Vol. 48, No. 7, Jul. 1, 2001, pp. 795-805.

Wagner, J., et al., "From Physiological Signals to Emotions: Implementing and Comparing Selected Methods for Feature Extraction and Classification," IEEE Int. Conf. Multimedia and Expo, Jan. 1, 2005, pp. 1-4.

Parkka, J., et al., "Activity Classification Using Realistic Data From Wearable Sensors," IEEE Transactions on Information Technology in Biomedicine, vol. 10, No. 1, Jan. 1, 2006, pp. 119-128.

Georgoulas, G., et al., "Predicting the Risk of Metabolic Acidosis for Newborns Based on Fetal Heart Rate Signal classification Using Support Vector Machines," IEEE Transactions on Biomedical Engineering, vol. 53, No. 5, May 1, 2006, pp. 875-884.

Liao, W., et al., "A Real-Time Human Stress Monitoring System Using Dynamic Bayesian Network," Proceedings of be 2005 IEEE Computer Society Conference on Computer Vision and Pattern Recognition, Jan. 1, 2005, pp. 1-8.

Moy, M., et al., "Accuracy of uniaxial accelerometer in chronic obstructive pulmonary disease," Journal of Rehabilitation Research and Development, vol. 45, No. 4, Nov. 4, 2008, pp. 611-618.

Moy, M., et al., "Ambulatory Monitoring of Cumulative Free-Living Activity," IEEE Engineering in Medicine and Biology Magazine May/Jun. 2003, May 1, 2003, pp. 89-95.

Ricke, AD, et al. "Automatic Segmentation of Heart Sound Signals Using Hidden Markov Models," IEEE Computers in Cardiology 2005; vol. 32, Jan. 1, 2005, pp. 953-956.

Acharya, R., et al., "Classification of cardiac abnormalities using heart rate signals," Medical and Biological Engineering and Computing 2004, vol. 42, No. 3, Jan. 1, 2004, pp. 288-293.

Allen, F., et al., "Classification of a known sequence of motions and postures from accelerometry data using adapted Gaussian mixture models," Institute of Physics Publishing Physiological Measurement, vol. 27, No. 10, Jul. 25, 2006, pp. 935-951.

Lee, J., et al., "Design of filter to reject motion artifact of pulse oximetry," Computer Standards & Interfaces, vol. 26 (2004), Jul. 4, 2003, pp. 241-249.

Rezek, I.A., et al., "Stochastic Complexity Measures for Physiological Signal Analysis," IEEE Transactions on Biomedical Engineering, vol. 45, No. 9, Sep. 1, 1998, pp. 1186-1191.

Gibbs, P., et al., "Active motion artifact cancellation for wearable health monitoring sensors using collocated MEMS accelerometers," Smart Struct. Mater., International Society for Optics and Photonics, Jan. 1, 2005, pp. 1-9.

Merletti, R., et al., "Advances in processing of surface myoelectric signals: Part 1," Medical and Biological Engineering and Computing, vol. 33, No. 3, May 1, 1995, pp. 362-372.

Asada, H., et al., "Active Noise Cancellation Using MEMS Accelerometers for Motion-Tolerant Wearable Bio-Sensors," Proceedings of the 26th Annual International Conference of the IEEE EMBS, San Francisco, CA, USA, Sep. 1, 2004, pp. 2157-2160.

Newman, A., et al., "Sleep Disturbance, Psychosocial Correlates, and Cardiovascular Disease in 5201 Older Adults: The Cardiovascular Health Study," Journal of American Geriatric Society, vol. 45, No. 1, Jan. 1, 1997, pp. 1-7.

Chan, K.W., et al., "Adaptive Reduction of Motion Artifact from Photoplethysmographic Recordings using a Variable Step-Size LMS Filter," IEEE, Sensors, Jun. 1, 2002, pp. 1342-1346.

Dew, M.A., et al., "Healthy Older Adults' Sleep Predicts All-Cause Mortality at 4 to 19 Years of Follow-Up," Psychosomatic Medicine, vol. 65, Jan. 1, 2003, pp. 63-73.

Gibbs, P., et al., "Reducing Motion Artifact in Wearable Bio-Sensors Using MEMS Accelerometers for Active Noise cancellation," IEEE American Control Conference, Jun. 1, 2005, pp. 1581-1586.

Yang, B-H, et al., "Development of the ring sensor for healthcare automation," Robotics and Autonomous Systems, vol. 30. Jan. 1, 2000, pp. 273-281.

Healey, J., et al., "Detecting Stress During Real-World Driving Tasks Using Physiological Sensors," IEEE Transactions on Intelligent Transportation Systems, vol. 6, No. 2, Jun. 1, 2005, pp. 156-166.

Hayes, M.J., et al., "A New Method for Pulse Oximetry Possessing Inherent Insensitivity to Artifact," IEEE Transactions on Biomedical Engineering, Vol. 48, No. 4, Apr. 1, 2001, pp. 452-461.

Wilson, G., et al., "An Analysis of Mental Workload in Pilots During Flight Using Multiple Psychophysiological Measures," The International Journal of Aviation Psychology, vol. 12, No. 1, May 1, 2001, pp. 3-18.

Baddeley, A.D., "Selective Attention and Performance in Dangerous Environments," HPEE, vol. 5, No. 1, Oct. 1, 2000, pp. 86-91.

Wilson, G.F., et al., "Performance Enhancement with Real-time Physiologically Controlled Adaptive Aiding," Proceedings of the IEA 2000 / HFES 2000 Congress, vol. 44, Jul. 30, 2000, pp. 61-64.

Skinner, M.J., et al., "Workload Issues in Military Tactical Airlift," The International Journal of Aviation Psychology, vol. 12, No. 1, May 1, 2001, pp. 79-93.

Helander, M., "Applicability of Drivers' Electrodermal Response to the Design of the Traffic Environment," Journal of Applied Psychology, vol. 63, No. 4, Jan. 18, 1978, pp. 481-488.

Perala, C.H., "Galvanic Skin Response as a Measure of Soldier Stress," Army Research Laboratory, ARL-TR-4114, May 1, 2007, pp. 1-35.

Zhai, J., et al., "Stress Detection in Computer Users Based on Digital Signal Processing of Noninvasive Physiological Variables," Conf Proc IEEE Eng Med Biol Soc., New York, NY, Aug. 31, 2006; pp. 1355-1358.

Zhai, J. et al., "Stress Recognition Using Non-invasive Technology," Flairs Conference, Melbourne Beach, Florida, May 11, 2006, AAAI Press, pp. 395-401.

Endler, J., "Signals, Signal Conditions, and the Direction of Evolution," The American Naturalist, vol. 139, Supplement, Mar. 1, 1992, pp. S125-S153.

Sadeh, A., "The role of actigraphy in sleep medicine," Sleep Medicine Reviews, vol. 6, No. 2, Jan. 1, 2002, pp. 113-124.

Declaration of Brian W. Anthony, Ph.D. In Support of Petition for Inter Partes Review of J.S. Patent 9,044,180, Exhibit 1003, Petition for Inter Partes Review of U.S. Pat. No. 9,044,180; *Apple, Inc. (Petitioner) v. Valencell, Inc. (Patent Owner)*, IPR 2017-01947, filed Aug. 15, 2-17, pp. 1-153.

Mendelson, J., et al., "Measurement Site and Photodetector Size Considerations iin Optimizing Power consumption of a Wearable Reflectance Pulse Oximeter", Proceedings of the 25th Annual

(56) References Cited

OTHER PUBLICATIONS

International Conference of he IEEE EMBS, Engineering in Medicine and Biology Society, Cancun, Mexico, Sep. 17, 2003, pp. 1-4.
Palder, et al., "Vascular Access for Hemodialysis, Patency rates and Results of Revision", Annals of Surgery, vol. 202, No. 2, Aug. 1, 1985, pp. 1-5.
Spigulis, J., et al., "Wearable wireless photoplethysmography sensors," Biophotonics: Photonic Solutions for Better -lealth Care, Proceedings of SPIE, vol. 6991, dated May 1, 2008, pp. 1-7.
Sandberg, M., et al., "Non-invasive monitoring of muscle blood perfusion by photoplethysmography: evaluation of a new application," Acta Physiol Scand., vol. 183, No. 4, Dec. 7, 2004, pp. 335-343.
Sum, K.W., et al. "Vital Sign Monitoring for Elderly at Home: Development of a Compound Sensor for Pulse Rate and Motion," Studies in Health Technology and Informatics, Personalised Health Management Systems, IOS Press, Jan. 1, 2005, pp. 43-50.
Mendelson, Y., et al., "A Wearable Reflectance Pulse Oximeter for Remote Physiological Monitoring," Proceedings of the 28th IEEE EMBS Annual International Conference New York City, USA, Aug. 30, 2006, pp. 912-915.
Jung, W., "Chapter H: OP Amp History," Op Amp Applications Handbook, published by Newnes/Elsevier, dated Jan. 1, 2005, ISBN-0/7506-7844-5, pp. H.1-H.72.
Texas Instruments, "General Purpose Operational Amplifiers", SLOSS094B, Nov. 1, 1970, pp. 1-19.
Schmitt, O., "A simple differential amplifier," Review of Scientific Instruments vol. 8, No. 126, dated Apr. 1, 1937, American Institute of Physics, pp. 1-3, available at: http://dx.doi.org/10.1063/1.1752256.
Gray, P, et al., "Recent Advances in Monolithic Operational Amplifier Design," IEEE Transactions on Circuits and Systems, vol. CAS-21, No. 3, May 1, 1974, pp. 317-327.
Horowitz, P., et al., "The Art of Electronics," Second Edition, Cambridge University Press, Jan. 1, 1989, pp. 98-102.
Petition for Inter Partes Review of U.S. Pat. No. 9044180; *Apple, Inc. (Petitioner)* v. *Valencell, Inc. (Patent Owner)*, IPR 2017-01947, filed Aug. 15, 2017, pp. 1-86.

\* cited by examiner

|  | SYSTOLIC (PULSE WAVE) | DIASTOLIC (INTERNAL) | PULSE-FIRST (DERIVATIVE) |
|---|---|---|---|
| INPUT NODES | 125 | 125 | 125 |
| HIDDEN NODES, LAYER 1 | 62 | 125 | 62 |
| HIDDEN NODES, LAYER 2 | n/a | n/a | 3 |
| OUTPUT NODES | 1 | 1 | 1 |
| TRAINING EPOCHS | 500 | 1000 | 1500 |
| COEFFICIENTS | 7,813 | 15,751 | 23,316 |
|  | (63+7750) | (126+15625) | (66+3*7750) |
| KB REQUIRED MEMORY | 31 | 63 | 93 |

FIG. 14

CORRELATION COEFFICIENTS OF NEURAL NETWORK MODEL AGAINST THE VALIDATION DATA (24 POINTS)

| PARAMETER | WAVE | FIRST DERIVATIVE | SECOND DERIVATIVE | INTEGRAL | ALL FOUR | "BEST TWO" (BOLD) |
|---|---|---|---|---|---|---|
| SYSTOLIC PRESSURE | 0.78 | 0.68 | 0.70 | 0.73 | 0.75 | 0.79 |
| DIASTOLIC PRESSURE | 0.65 | 0.74 | 0.75 | 0.76 | 0.68 | 0.79 |
| PULSE PRESSURE | 0.68 | 0.78 | 0.28 | 0.50 | 0.72 | 0.71 |

FIG. 15

METHOD AND APPARATUS FOR GENERATING ASSESSMENTS USING PHYSICAL ACTIVITY AND BIOMETRIC PARAMETERS

BACKGROUND

A personal health monitor provides a user with the ability to monitor his overall health and fitness by enabling the user to monitor heart rate and/or other biometric information during exercise, athletic training, rest, daily life activities, physical therapy, etc. Such devices are becoming increasingly popular as they become smaller and more portable.

In addition to providing biometric information such as heart rate and breathing rate, a personal health monitor may also provide physical activity information, e.g., duration, distance, cadence, etc. As with the sensing or measurement of many parameters, however, the accurate determination of such information may be compromised by noise.

A user's cadence enables the user to monitor his current performance relative to his personal goals, and therefore represents a particularly useful physical activity parameter. As used herein, a cadence represents the number of repetitions per minute of some physical activity. For example, when the user is moving on foot, the cadence represents the number of foot repetitions or steps per minute. When the user is moving on wheels, the cadence represents the number of cycle repetitions (e.g., crank or pedal revolutions) per minute.

Conventional devices may monitor the cycling cadence, for example, using a cyclocomputer. A sensor system mounted to the crank arm and frame of the bicycle counts the number of pedal rotations per minute to determine the cycling cadence. While such devices are useful and reasonably accurate, they are cumbersome and cannot easily be used with multiple bicycles. Further, such devices cannot provide an accurate estimate of the number of steps per minute taken, e.g., by a runner. Further still, such devices generally do not provide additional performance information, e.g., calories burned, at least not with a desired degree of accuracy.

In addition, there is an increased desire for everyday users to have easy access to information regarding their exercise routine and/or the results of their exercise routine, regardless of the exercise conditions or circumstances. For example, the speed of a runner jogging through a neighborhood may easily be determined by using a Global Positioning System (GPS). When the user jogs on a treadmill, however, GPS is useless. In another example, it may be desired to determine a user's maximum oxygen consumption/uptake/aerobic capacity ($VO_2$max) without subjecting the user to costly and time consuming tests in a laboratory set up for just such testing.

Thus, there remains a need for more portable devices wearable by a user and capable of accurately measuring and/or estimating biometric and/or physical activity parameters (e.g., heart rate and/or speed), and any associated physiological assessment parameters (e.g., $VO_2$max), in a wide variety of scenarios.

SUMMARY

The solutions presented herein provide methods and apparatus for the determination and/or improved quality of one or more physiological assessment parameters based on biometric signal(s) and/or motion signal(s) respectively output by one or more biometric and/or motion sensors. Exemplary biometric parameters include, but are not limited to, heart rate, breathing rate, breathing volume, blood pressure, pulse pressure, response-recovery interval, and heart rate variability. Exemplary physiological assessment parameters include, but are not limited to, a user cadence and a user speed.

One exemplary method determines a physiological assessment parameter associated with a user using an activity monitoring device comprising at least one biometric sensor and at least one motion sensor, where at least the biometric sensor contacts the user's skin. The method comprises processing a motion signal output by the motion sensor over a first period of time to determine a physical activity parameter for the user over the first period of time, and processing a biometric signal output by the biometric sensor over the first period of time to determine a biometric parameter for the user over the first period of time. The method further comprises determining the physiological assessment parameter based on the physical activity parameter and the biometric parameter.

One exemplary apparatus comprises an assessment generation system configured to determine a physiological assessment parameter associated with a user via at least one biometric sensor and at least one motion sensor comprised in an activity monitoring device disposed proximate the user such that the biometric sensor contacts the user's skin. The assessment generation system comprises a motion processing circuit, a biometric processing circuit, and an assessment processing circuit. The motion processing circuit is configured to process a motion signal output by the motion sensor over a first period of time to determine a physical activity parameter for the user over the first period of time. The biometric processing circuit is configured to process a biometric signal output by the biometric sensor over the first period of time to determine a biometric parameter for the user over the first period of time. The assessment processing circuit is configured to determine the physiological assessment parameter based on the physical activity parameter and the biometric parameter.

Another exemplary method estimates a speed of a user via a wearable activity monitoring device disposed proximate the user and comprising a motion sensor. The method comprises processing a motion signal output by the motion sensor to determine a type of user motion, and processing the motion signal based on the determined type of user motion to determine a physical activity parameter. The method further comprises estimating a stride length of the user based on the motion signal and the determined type of user motion, and estimating the speed of the user based on the physical activity parameter and the stride length.

Another exemplary apparatus comprises an assessment processing circuit for estimating a speed of a user via an activity monitoring device disposed proximate the user. The activity monitoring device comprises a motion sensor. The assessment processing circuit is configured to process a motion signal output by the motion sensor to determine a type of user motion, and process the motion signal based on the determined type of user motion to determine a physical activity parameter. The assessment processing circuit is further configured to estimate a stride length of the user by processing the motion signal based on the determined type of user motion, and estimate the speed of the user based on the physical activity parameter and the stride length.

Another exemplary method improves an accuracy of at least one of an estimated biometric parameter and an estimated physiological assessment parameter determined for a current period of time and associated with a user wearing an activity monitoring device. The activity monitoring device comprises at least one motion sensor. The method comprises generating a personalized biometric model for the user based on one or more biometric parameters and one or more physical activity parameters determined for a second period of time previous to the current period of time, and processing a motion signal output by the motion sensor to determine a current physical activity parameter for the user for the current period of time. The method further comprises processing the current physical activity parameter based on the personalized biometric model to improve the accuracy of at least one of the estimated biometric parameter and the estimated physiological assessment parameter determined for the user for the current period of time.

Another exemplary apparatus comprises an assessment processing circuit configured for improving an accuracy of at least one of an estimated biometric parameter and an estimated physiological assessment parameter determined for a current period of time and associated with a user wearing an activity monitoring device. The activity monitoring device comprises at least one motion sensor operatively connected to the assessment processing circuit. The assessment processing circuit is configured to generate a personalized biometric model for the user based on a history of one or more biometric parameters and one or more physical activity parameters determined for a second period of time previous to the current period of time, and process a motion signal output by the motion sensor to determine a current physical activity parameter for the user for the current period of time. The assessment processing circuit is further configured to process the current physical activity parameter based on the personalized biometric model to improve the accuracy of at least one of the estimated biometric parameter and the estimated physiological assessment parameter determined for the user for the current period of time.

BRIEF DESCRIPTION OF THE DRAWINGS

FIG. 14 shows optimal neural network details for exemplary single-representation models.

FIG. 15 show exemplary details associated with generating a model used by the assessment system of FIG. 7.

DETAILED DESCRIPTION

Figure 1:
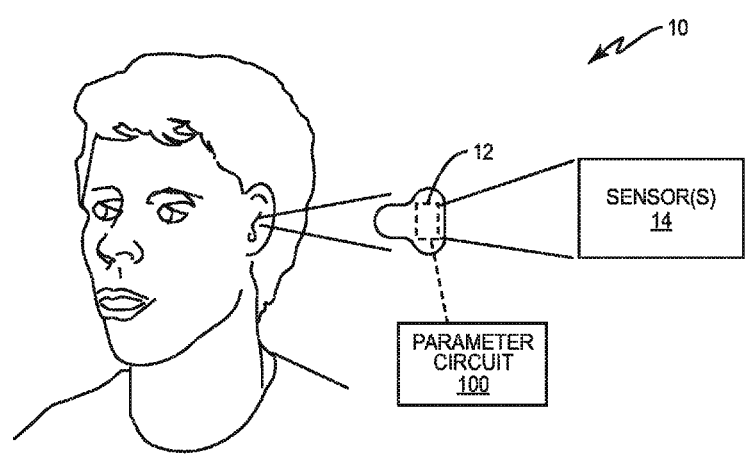
FIG. 1 shows an exemplary cadence measurement system disposed in an ear bud.

The measurement techniques and processors disclosed herein provide an accurate measurement of one or more biometric, physical activity, and/or physiological assessment parameters (e.g., values) based on a signal provided by a motion sensor disposed proximate a user's body. As used herein, the term "processor" broadly refers to a signal processing circuit or computing system, or processing or computing method, which may be localized or distributed. For example, a localized signal processing circuit may comprise one or more signal processing circuits or processing methods localized to a general location, such as to an activity monitoring device. Examples of such monitoring devices may comprise an earpiece, a headpiece, a finger clip, a toe clip, a limb band (such as an arm band or leg band), an ankle band, a wrist band, a nose band, a sensor patch, or the like. Examples of a distributed processing circuit comprise "the cloud," the internet, a remote database, a remote processor computer, a plurality of remote processing circuits or computers in communication with each other, etc., or processing methods distributed amongst one or more of these elements. The key difference between the distributed and localized processing circuits is that a distributed processing circuit may include delocalized elements, whereas a localized processing circuit may work independently of a distributed processing system. Microprocessors, microcontrollers, or digital signal processing circuits represent a few non-limiting examples of signal processing circuits that may be found in a localized and/or distributed system.

The term "parameter" as used herein broadly refers to any set of physical properties, measured value(s), or processed information whose value(s) collectively relate the characteristics and/or behavior of something. A "parameterization" refers to the generation of at least one parameter from a set of data. For example, a biometric parameter, also referred to herein as a physiological parameter, represents a physiological function of an organism. Exemplary biometric parameters include, but are not limited to, a heart rate, breathing rate, breathing volume, blood pressure, pulse pressure, R-R interval (time interval between successive "R" peaks of a cardiac cycle, e.g., as shown in a QRS complex of an electrocardiogram), heart rate variability, body temperature (e.g., core temperature, gut temperature, electrical or thermal conductivity in the body or skin of an organism, tympanic temperature, skin temperature, etc.), brain wave activity, energy expenditure (e.g., calories burned), ECG activity, a parameterization of sampled data from the at least one physiological sensor, or the like.

A physical activity parameter represents a parameter relating to a physical activity of an organism. Exemplary physical activity parameters include, but are not limited to, a motion parameter e.g., a walking cadence, running cadence, sprinting cadence, cycling cadence, limb cadence, walking speed, running speed, cycling speed, limb motion speed, head motion, a parameterization of sampled data from the at least one motion sensor, or the like. Examples of a parameterization of digitally sampled data from a motion sensor (e.g., an accelerometer) include, but are not limited to, filtering (low-pass, high-pass, bandwidth, notch, etc.) of each accelerometer axis, processing the sampled data to generate root-mean-squared (RMS) sampled data (e.g., squaring the sampled data from each accelerometer axis, summing the result, and taking the square root of the sum), tracking the maximum values of sampled data or processed sampled data over a period of time and averaging the result, generating at least one spectral transform of the sampled data, identifying maximums or minimums in the sampled data, applying a function to the sampled data (e.g., a derivative function, integral function, trigonometric function, etc.).

As used herein, the "cadence" refers to the number of repetitions or complete cycles per unit of time, e.g., cycles per minute. Exemplary cadences include, but are not limited to, a step rate (e.g., the number of steps or foot repetitions per minute), a cycle rate (e.g., the number of pedaling cycles or cycle revolutions per minute), a repetition rate (e.g., with respect to lifting weights), etc. It will be appreciated that a step cadence may represent the user's cadence while walking, running, doing aerobics, climbing stairs, etc. Further, it will be appreciated that a cadence may refer to movement by mobile animals or machinery, e.g., a walking robot. Exemplary animals include, but are not limited to, biped animals (e.g., humans, birds, etc.) and quadruped animals (e.g., dogs, horses, etc.).

A physiological assessment parameter represents an assessment of a biometric/physiological function, e.g., the health or fitness level of an organism and/or efficiency of a machine. Exemplary physiological assessment parameters include, but are not limited to, an assessment of aerobic fitness level, $VO_2$max, cardiovascular health, heart rate recovery time, endurance level, physical strength, exercise efficiency, running efficiency, biometric identification, a parameterization of sampled data from at least at least two other parameters (biometric parameters and/or physical activity parameters, for example).

More broadly, a biometric parameter may include an acute (instantaneous) measurement of a biometric signal, such as an acute body temperature measurement, and/or a processed collection of measurements of a biometric signal, e.g., measurements of heart rate over time by processing a PPG waveform over time. A physical activity parameter may include an acute measurement of a motion signal, e.g., an acceleration, and/or or a processed collection of measurements of a motion signal, e.g., accelerometer values processed from multiple axes over a period of time to identify the peak acceleration over a period of time. A physiological assessment parameter may include an acute measurement of two or more parameters (e.g., biometric parameters and/or physical activity parameters). For example, a physiological assessment parameter may include a measurement of a current user cadence and heart rate, and/or a processed collection of measurements of parameters over a period of time, e.g., a ratio of average cadence and average breathing rate generated over the course of a 30 minute treadmill run. In some cases, any one or more of these parameters may be the same as, or substantially the same as, a well-defined, well-established behavior, measurement, assessment, or classification. For example, a physiological assessment parameter that comprises a ratio of the change in heart rate ($\Delta H$) and the change in time ($\Delta t$) over the course of 1-minute of rest following exercise is commonly referred to as "1-minute heart rate recovery." In this case, the measured physiological assessment parameter (the ratio $\Delta H/\Delta t$) is the same as the established physiological assessment (1-minute heart rate recovery).

It will be appreciated that a physiological assessment parameter may be generated by processing physical activity parameter(s) and/or biometric parameter(s). For example, an assessment of a person's overall health may be determined by processing concurrent cadence (activity parameter) information and $VO_2$max (physiological assessment parameter) information. More specifically, maintaining a relatively high (for one's own demographic) $VO_2$max over a period of time, with respect to one's average daily cadence, may be indicative of good overall health. Similarly, a person may be identified from other persons with the aid of a sufficiently unique $VO_2$max/cadence pattern observed over a period of time. The term "biometrics" refers broadly to a plurality of biometric parameters and/or physiological assessment parameters.

As used herein, the terms "inertia" or "inertial" refer broadly to "motion," and an inertial sensor refers to a motion sensor.

FIG. 1 shows part of an exemplary measurement system 10, where one or more sensors 14 are disposed in an ear bud 12, and a parameter circuit 100 is operatively connected to the sensor(s) 14, e.g., via a wired or wireless connection. The parameter circuit 100 may be secured to the user, e.g., via a clip. The ear bud 12 may comprise a wireless or wired ear bud that communicatively couples to a remote device (not shown), e.g., a music player, a smart phone, a personal data assistant, etc. While not required, it will be appreciated that the parameter circuit 100 may be disposed in the remote device. While FIG. 1 shows the sensor(s) 14 as being part of an ear bud 12, it will be appreciated that the sensor(s) 14 may be disposed in any wearable device that secures to the body of a user, e.g., a device that secures to an ear, finger, toe, limb, ankle, wrist, nose, etc. In some embodiments, the device may comprise a patch, e.g., a bandage, designed to attach the system 10 to any desired location on the user's body. While FIG. 1 shows the parameter circuit 100 as being separate from the ear bud 12, it will be appreciated that part or all of the parameter circuit 100 may be disposed in the ear bud 12

Measurement system 10 measures one or more parameters particular to the user wearing the ear bud 12, e.g., biometric, physical activity, and/or physiological assessment parameters. The measurement system 10 outputs the measured parameter(s) to the user and/or to other processing functions or elements.

Figure 2:
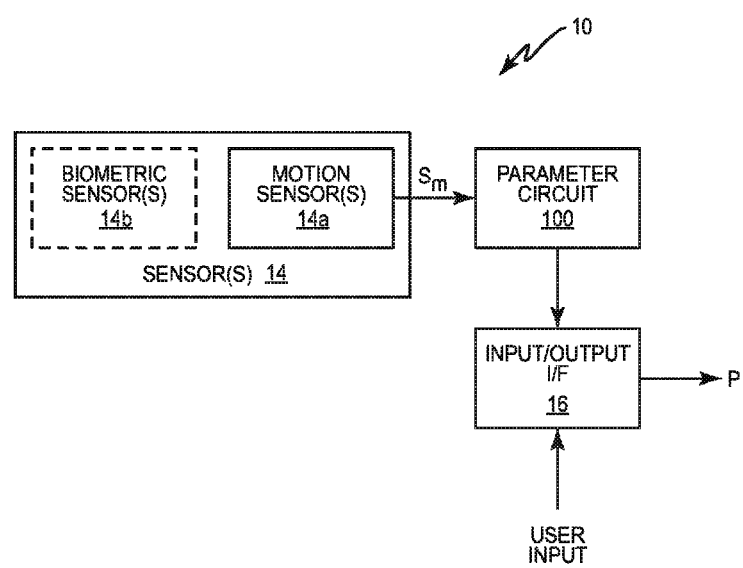
FIG. 2 shows a block diagram of an exemplary measurement system.

FIG. 2 shows a block diagram of an exemplary measurement system 10 according to one exemplary embodiment. System 10 comprises the parameter circuit 100 coupled to one or more sensors 14 and an input/output interface 16, where the sensor(s) 14 include at least one motion sensor 14a, and an optional biometric sensor 14b. It will be appreciated that the motion sensor 14a may incorporate biometric sensor or physiological sensor capabilities. Motion sensor 14a is configured to sense energy, e.g., motion, external to the system 10, and to output a motion signal $S_m$ representative of the sensed energy, e.g., proportional to an acceleration of the user. The motion sensor 14a may comprise a single axis sensor or a multiple axis sensor. Exemplary motion sensors 14a include but are not limited to accelerometers, Micro-Electro-Mechanical System (MEMS) devices, gyroscopes, optical sensors, an opto-mechanical sensor, a blocked channel sensor (e.g., as shown in US2010/0217102), a capacitive sensor, and a piezo sensor. When the motion sensor 14a comprises a multiple axis sensor, frequency and power information from each axis may be combined or otherwise evaluated to determine the desired information, e.g., the peak frequency and the motion power. For example, the spectral magnitude may be determined for each axis, where a maximum one of the spectral magnitudes, a sum of the squares, a maximum of the squares, a sum of the absolute values, a maximum of the absolute values, the root-sum-squares, the root-mean-squares, and/or the decimation of the spectral magnitudes is ultimately used to determine the motion power and to identify the peak frequency. Parameter circuit 100 processes the motion signal $S_m$ as disclosed herein to determine parameter(s) P. Input/output interface 16 provides input from the user to the parameter circuit 100, and outputs the determined parameter P. It will be appreciated that input/output interface 16 may include a display, a keyboard or other data entry device, and/or a transceiver for transmitting the cadence to a remote device. Alternatively or additionally, the input/output interface 16 may provide the cadence to the display, a database, a processing circuit, and/or a processing function.

Figure 3:
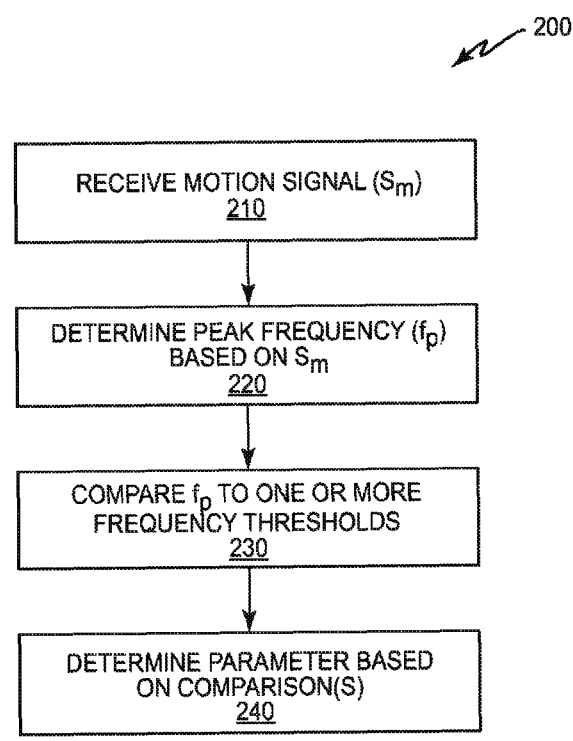
FIG. 3 shows an exemplary process for determining a parameter from data provided by a motion sensor.

FIG. 3 shows an exemplary method 200 that may be implemented by the measurement system 10 to determine a parameter P. After the parameter circuit 100 receives the motion signal $S_m$ from the motion sensor 14a (block 210), the parameter circuit 100 determines a peak frequency $f_p$ based on $S_m$ (block 220). The peak frequency $f_p$ represents the frequency component of the motion signal $S_m$ having the largest amplitude. The parameter circuit 100 subsequently applies the peak frequency $f_p$ to one or more frequency threshold comparisons (block 230). Based on the frequency threshold comparisons, the parameter circuit 100 determines the parameter(s) P, e.g., a user cadence C (block 240).

Figure 4:
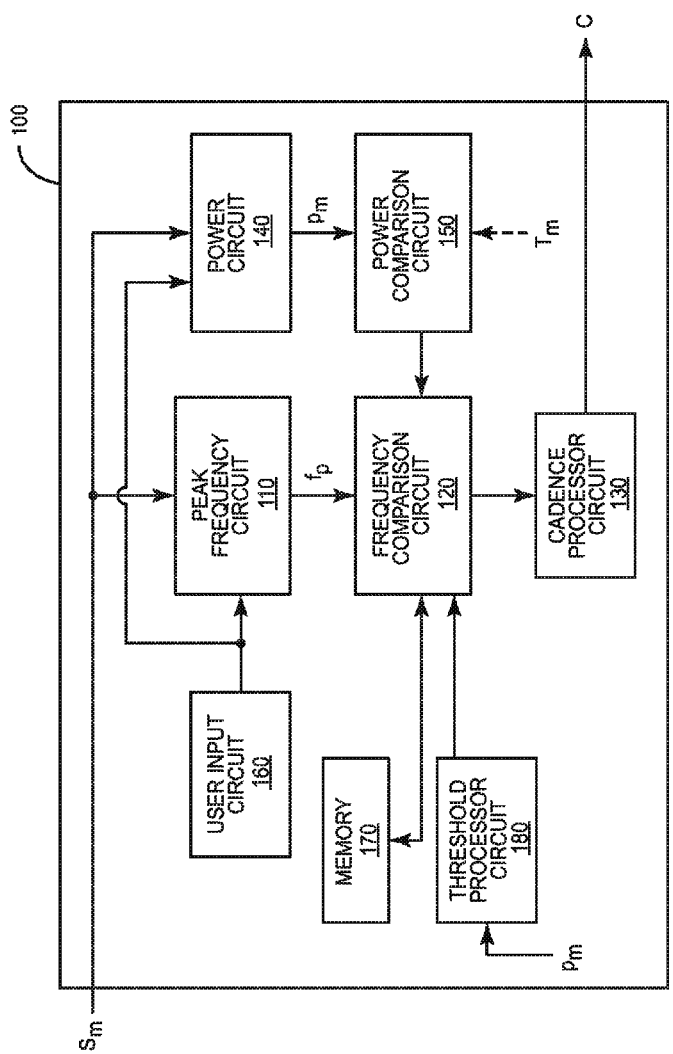
FIG. 4 shows a block diagram of an exemplary parameter circuit.

FIG. 4 shows a block diagram of an exemplary parameter circuit 100 configured to determine a user cadence C from the motion signal output by the motion sensor 14a. Parameter circuit 100 comprises a peak frequency circuit 110, a frequency comparison circuit 120, and a cadence processor circuit 130. Peak frequency circuit 110 determines the peak frequency of the input motion signal. The frequency comparison circuit 120 applies the peak frequency to one or more frequency threshold comparisons. The cadence processor circuit 130 determines the user cadence based on the peak frequency and the one or more frequency threshold comparisons.

The peak frequency circuit 110 identifies the frequency component of the motion signal having the largest signal amplitude. In one exemplary embodiment, peak frequency circuit 110 may achieve this goal by performing a frequency transform of the motion signal to determine a spectral signal. The peak frequency circuit 110 then identifies the frequency component of the spectral signal having the largest amplitude as the peak frequency. It will be appreciated that other means, e.g., phase-locked loop, pulse picking, or time-domain implementations, may be used to determine the peak frequency.

Figure 5:
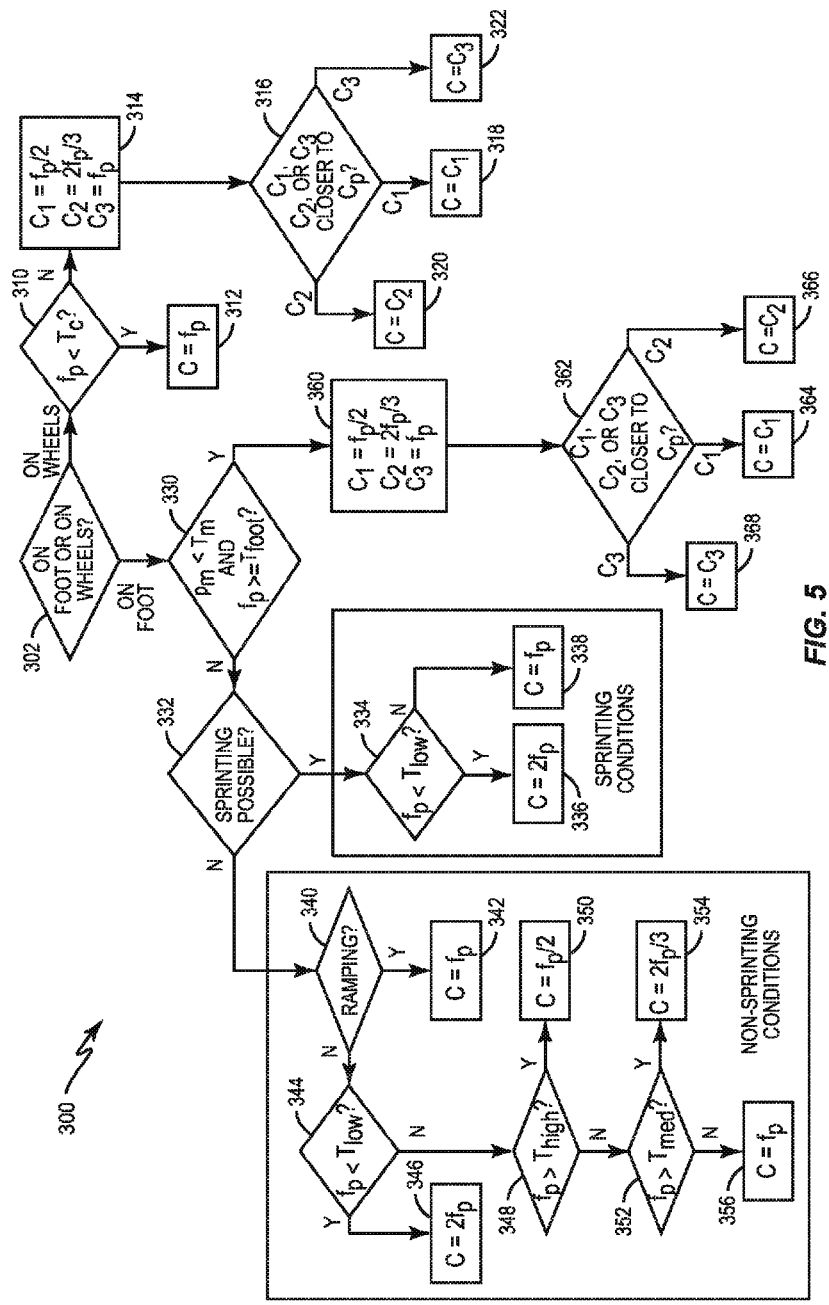
FIG. 5 shows a more detailed process for determining a user cadence from data provided by a motion sensor according to one exemplary embodiment.

The frequency comparison circuit 120 applies the peak frequency to one or more frequency threshold comparisons. The frequency peak often corresponds directly to the user cadence. However, in some instances, the user cadence is some harmonic factor of the peak frequency. Empirical research shows the peak frequency is often twice, half, or three-halves the user cadence. As shown in FIG. 5, when sprinting is possible the typical walking harmonics are $2 f_p$, $\frac{3}{2} f_p$, or $\frac{1}{2} f_p$ and the typical running harmonics are $\frac{1}{2} f_p$. For example, harmonics at $2 f_p$ and $\frac{3}{2} f_p$ often occur when the user walks, but not when the user runs. Thus, the cadence may actually be $\frac{1}{2} f_p$ or $\frac{2}{3} f_p$, respectively. When the user runs, harmonics at $\frac{1}{2} f_p$ often occur. Thus, the cadence in this scenario may actually be $2 f_p$, $\frac{2}{3} f_p$, or $\frac{1}{2} f_p$. Thus, the cadence circuit 100 must determine which harmonic factor, if any, is applicable to determining the current user cadence.

The frequency threshold comparisons applied by the frequency comparison circuit 120 as disclosed herein solve this problem using one or more threshold comparisons, where the thresholds are determined based on a previous user cadence, a power of the motion signal, user activity parameters, user information, and/or empirical values. It will be appreciated that different harmonic factors and/or thresholds may apply depending on whether the user is sprinting, walking, running, ramping up from a low frequency value, cycling, etc. For example, harmonic factors due to arm swing, head bobbing, etc., impact the user cadence differently depending on how the user is moving, e.g., whether the user is running or walking. Thus, the cadence circuit 100 may optionally comprise a power circuit 140, a power comparison circuit 150, a user input circuit 160, a memory 170, and/or a threshold processor circuit 180 that determine and/or provide the various harmonic factors and thresholds necessary to determine the user cadence.

The power circuit 140 is configured to determine the motion power (e.g., the inertial power) $p_m$ of the motion signal. To that end, the power circuit 140 may compute $p_m$ in the time domain, e.g., using the root mean square, or in the frequency domain, e.g., using the amplitude of a spectral peak. The power comparison circuit compares $p_m$ to a power threshold $T_m$ to facilitate the determination of whether the user is running or walking. User input circuit 160 receives input from the user. The user input may be used to determine one or more user activity parameters, e.g., whether the user is on foot or on wheels, whether sprinting is possible, etc. Threshold processor circuit 180 is configured to determine one or more of the thresholds used by the frequency comparison circuit 120, including any frequency thresholds used to determine a running cadence, a walking cadence, a cycling cadence, etc., and the power threshold used by the power comparison circuit 150. Memory 170 stores any predetermined thresholds, one or more previously determined cadences $C_p$, the various harmonic factors used by the cadence processor circuit 130, and any other information or software necessary for successful operation of the parameter circuit 100.

FIG. 5 shows an exemplary detailed process 300 executed by the parameter circuit 100 to determine the user cadence C. As shown by FIG. 5, parameter circuit 100 determines the user cadence based on the peak frequency and one or more frequency threshold comparisons. In exemplary embodiments, the parameter circuit 100 determines a user activity parameter, and determines the user cadence based on the frequency threshold comparison(s) and the user activity parameter. For example, the physical activity parameter may identify whether the user is on foot or on wheels (block 302). When on wheels, the frequency comparison circuit 120 compares the peak frequency $f_p$ to a cycling threshold $T_c$, which may be fixed or variable based on a power of the motion signal (block 310). When $f_p < T_c$, the cadence processor circuit 130 sets the cadence equal to the peak frequency (block 312). Otherwise, the cadence processor circuit 130 generates two or more test cadences, and sets the user cadence equal to the test cadence closest to a previous user cadence (blocks 314-322). For example, the cadence processor circuit 130 may generate three test cadences: $C_1 = \frac{1}{2} f_p$, $C_2 = \frac{2}{3} f_p$, and $C_3 = f_p$ (block 314), and compare the three test cadences to a previous user cadence $C_p$ (block 316). If $C_1$ is closer to $C_p$ than $C_2$ or $C_3$ are, the cadence processor circuit 130 sets the user cadence equal to $C_1$ (block 318). If $C_2$ is closer to $C_p$ than $C_1$ or $C_3$ are, the cadence processor circuit 130 sets the user cadence equal to $C_2$ (block 320). If $C_3$ is closer to $C_p$ than $C_2$ or $C_1$ are, the cadence processor circuit 130 sets the user cadence equal to $C_3$ (block 322). While the example of FIG. 5 shows determining and using three specific test cadences, it will be appreciated that any two or more test cadences may be used.

When the user is on foot (block 302), the cadence processor circuit 130 sets the user cadence equal to the peak frequency divided by a harmonic factor, e.g., ½, 1, ⅔, 2, etc. More particularly, the cadence processor circuit 130 determines the user cadence based on frequency and power comparisons respectively performed by the frequency comparison circuit 120 and the power comparison circuit 150 (block 330). For example, when $p_m$ is less than $T_m$ and $f_p \geq T_{foot}$, cadence processor circuit 130 generates two or more test cadences based on $f_p$ and two or more of the harmonic factors, and determines the user cadence based on the test cadences and a previous user cadence (blocks 360-368). For example, the cadence processor circuit 130 may generate three test cadences: $C_1 = \frac{1}{2} f_p$, $C_2 = \frac{2}{3} f_p$, and $C_3 = f_p$ (block 360), and compare the three test cadences to a previous user cadence $C_p$ (block 362). If $C_1$ is closer to $C_p$ than $C_2$ or $C_3$ are, the cadence processor circuit 130 sets the user cadence equal to $C_1$ (block 364). If $C_2$ is closer to $C_p$ than $C_1$ or $C_3$ are, the cadence processor circuit 130 sets the user cadence equal to $C_2$ (block 366). If $C_3$ is closer to $C_p$ than $C_2$ or $C_1$ are, the cadence processor circuit 130 sets the user cadence equal to $C_3$ (block 368). While the example of FIG. 5 shows determining and using three specific test cadences, it will be appreciated that any two or more test cadences may be used.

However, when $p_m \geq T_m$ and/or $f_p < T_{foot}$, the cadence processor circuit 130 determines the user cadence based on frequency threshold comparison(s) and a sprinting user activity parameter, which indicates whether sprinting conditions are possible (blocks 332-356). More particularly, when $p_m \geq T_m$ and/or $f_p < T_{foot}$, the cadence processor circuit 130 determines whether sprinting conditions are possible based on user input (block 332). For example, the user may select an activity mode, e.g., walking, slow or low impact aerobics, high impact aerobics, running, etc. from a menu of options. Based on the selected activity mode, the cadence processor circuit 130 determines whether sprinting conditions are possible. For example, when the user selects slow aerobics, the cadence processor circuit 130 determines that sprinting is not possible. Alternatively, when the user selects running, the cadence processor circuit 130 determines that sprinting is possible. If sprinting conditions are possible, the cadence processor circuit 130 determines the user cadence based on a comparison between $f_p$ and a low frequency threshold $T_{low}$ under sprinting conditions (blocks 334-338). When $f_p < T_{low}$, the cadence processor circuit 130 sets the user cadence equal to the peak frequency divided by the ½ harmonic factor, e.g., equal to twice the peak frequency (block 336). Otherwise, the cadence processor circuit 130 sets the user cadence equal to the peak frequency (block 338).

If sprinting conditions are not possible, the cadence processor circuit 130 determines the user cadence based on multiple frequency threshold comparisons under non-sprinting conditions (blocks 340-356). More particularly, the cadence processor circuit applies the peak frequency to multiple thresholds based on whether the peak frequency is ramping up from a low frequency value (block 340), and determines the user cadence based on that ramping information and the frequency threshold conditions (blocks 342-356). While not required, in some exemplary embodiments, the low frequency value is zero. During non-sprinting conditions when the peak frequency is ramping up from a low frequency value, the cadence processor circuit 130 sets the user cadence equal to the peak frequency (block 342).

However, during non-sprinting conditions when the peak frequency is not ramping up from a low frequency value, the cadence processor circuit 130 determines the user cadence based on multiple peak frequency threshold comparisons determined by the frequency comparison circuit 120 under non-sprinting conditions relative to a low frequency threshold $T_{low}$, an intermediate frequency threshold $T_{med}$, and a high frequency threshold $T_{high}$, where $T_{low} < T_{med} < T_{high}$ (blocks 344-356). More particularly, under these conditions when $f_p < T_{low}$ (block 344), the cadence processor circuit 130 sets the user cadence equal to the peak frequency divided by the ½ harmonic factor, e.g., equal to twice the peak frequency (block 346). When $f_p \geq T_{low}$ and $f_p > T_{high}$ (blocks 344 and 348), the cadence processor circuit 130 sets the user cadence equal to the peak frequency divided by the 2 harmonic factor, e.g., equal to half the peak frequency (block 350). When $f_p \geq T_{low}$ and $f_p \leq T_{high}$ and $f_p < T_{med}$ (blocks 344, 348, and 352), the cadence processor circuit 130 sets the user cadence equal to the peak frequency divided by the ⅔ harmonic factor, e.g., equal to two-thirds the peak frequency (block 354). Otherwise, the cadence processor circuit 130 sets the user cadence equal to the peak frequency (block 356).

As discussed herein, parameter circuit 100 determines the user cadence based on one or more frequency threshold comparisons. Each frequency threshold, as well as the power threshold, may be determined empirically or based on one or more parameters, e.g., a previous user cadence, a power of a motion signal, user information, and/or a physical activity parameter. For example, the cycling threshold $T_c$ and/or the foot threshold $T_{foot}$ may be determined empirically based on observation, and/or based on user input information, user activity parameter, and/or $p_m$. In one exemplary embodiment, for example, the foot threshold may be determined according to:

$$T_{foot} = 120 + 40 \frac{p_m}{T_m}. \tag{1}$$

An exemplary cycling threshold $T_c$ is 100 revolutions per minute, while an exemplary foot threshold $T_{foot}$ is 145 steps per minute. The power threshold $T_m$ and/or the low threshold may be determined empirically and/or based on user information, e.g., the user's weight, shoe sole compliance information, etc., $p_m$, a previous user cadence, and/or user activity parameters. In one exemplary embodiment, $T_{low} = 60$ (a constant). It has been shown, for example, that the low frequency threshold is more accurate when determined as a function of $p_m$. For example, when $p_m \leq T_m$, the low threshold may be determined based on $p_m$ according to:

$$T_{low} = 60 + 20 \frac{p_m}{T_m}. \tag{2}$$

When $p_m > T_m$, alternatively, $T_{low}$ may be set equal to 80. In another exemplary embodiment, the low threshold may be determined based on the previous user cadence according to:

$$T_{low} = 0.6 C_p. \quad (3)$$

It will be appreciated that different values for $T_{low}$ may be used for different scenarios. Thus, a combination of the above-disclosed options may be selectively used depending on the different scenarios, e.g., whether $p_m > T_m$. Similarly, the intermediate and high thresholds may be determined based on a previous user cadence and/or $p_m$. For example, the intermediate and high thresholds may be determined as a function of the previous user cadence and a sprint factor. The sprint factor for the intermediate threshold may be determined empirically, e.g., based on 1.75 or 1.4 times the previous user cadence. It will be appreciated that each threshold may be fixed or variable. It will also be appreciated that the frequency thresholds (e.g., $T_c$, $T_{foot}$, $T_{low}$, $T_{med}$, $T_{high}$) and the power threshold ($T_m$) discussed herein are exemplary and non-limiting; other thresholds may be used depending on the system configuration, the information available to the parameter circuit 100, etc.

The user cadence method and apparatus disclosed herein accurately determines a user cadence for a wide range of circumstances and environments. Further, because the user may wear the hardware necessary to implement this solution, the solution disclosed herein is applicable for any user activity, including cycling, walking, running, athletic training, sports, aerobics, weight lifting or any other repetitive exercises, jumping, etc.

Figure 6A:
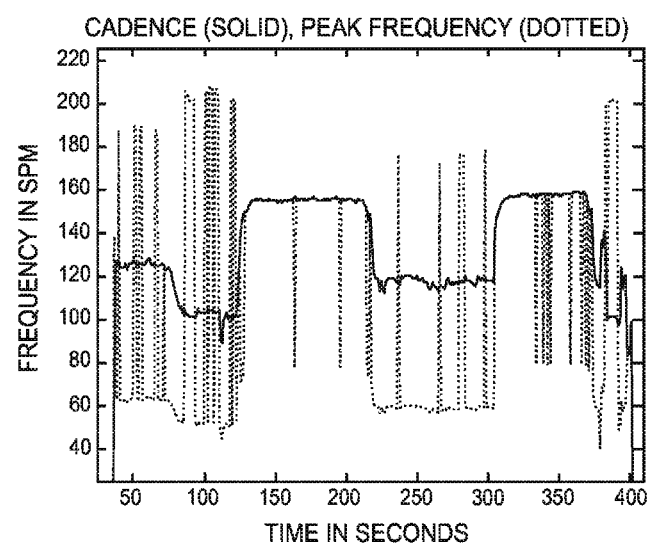
FIGS. 6A and 6B show simulation results associated with the disclosed solution.
Figure 6B:
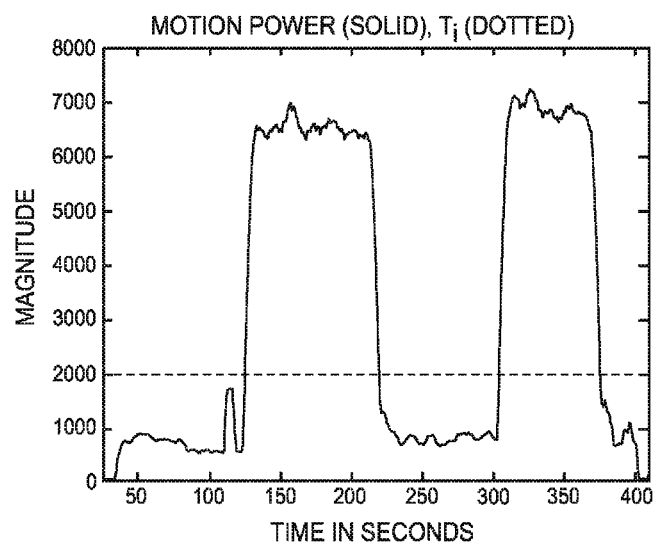

FIGS. 6A and 6B show simulated results for one exemplary implementation of the measurement 10 system disclosed herein. The plots shown in FIGS. 6A and 6B are generated from the same data set produced by an individual running and walking on a treadmill. FIG. 6A shows the user cadence with respect to time as computed according to FIG. 5 using the spectral peak frequency provided by the motion sensor 14a. FIG. 6B shows the power output by the motion sensor 14a with respect to time. FIG. 6B also shows an exemplary power threshold $T_m$ of 2000, which is used to determine whether the user is running or walking/resting. The units for the y-axis circuits FIG. 6B are "g's" scaled by a systematic multiplier, where 1 g is the force of gravity on Earth at sea level. As shown by FIGS. 6A and 6B, the user is running from 125-215, seconds and from 300-375 seconds. Thus, in these regions, user cadence method and apparatus disclosed herein avoids mistaking the peak frequencies above 145 steps per minute as 2× or ³⁄₂× harmonics. The 40-70 seconds region shows ³⁄₂× and ½× harmonics, the 80-120 seconds region shows 2× and ½× harmonics, and the 125-215 seconds region shows ½× harmonics. All of these harmonics, when divided by the corresponding harmonic factor as disclosed herein, produce the correct user cadence.

In some embodiments, measurement system 10 may also comprise additional sensors. For example, the measurement system 10 may include additional biometric sensors 14b, e.g., blood flow (photoplethysmography (PPG)), body temperature, and/or heart rate sensors, that contact at least some of the user's skin.

Figure 7:
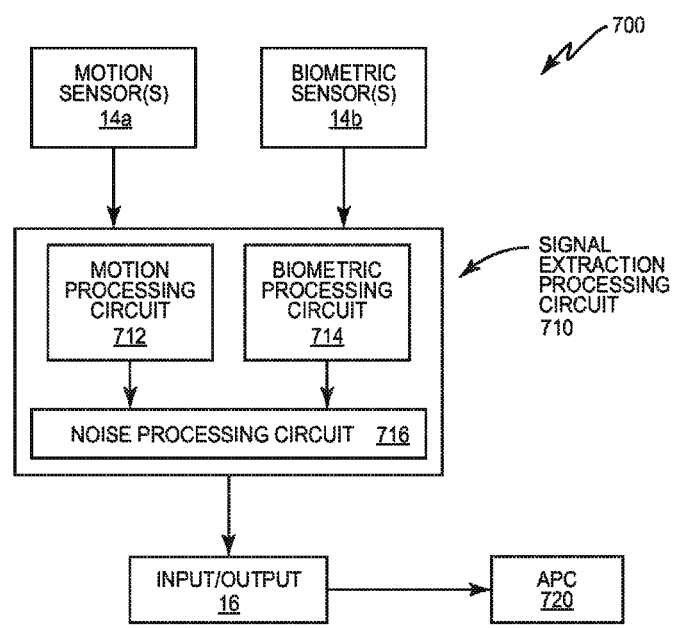
FIG. 7 shows a block diagram of an exemplary assessment system.

In some embodiments, the measurement system 10 may be part of an assessment generation system 700, e.g., as shown in FIG. 7 for the purpose of generating physiological assessments of a user. The assessment generation system 700 may comprise the sensors 14 and input/output 16 of FIG. 2, as well as a signal extraction processing circuit 710. The key purpose of the signal extraction processing circuit is to attenuate and/or remove unwanted noise from at least one of the sensors 14 and, optionally, to generate at least one accurate physical activity (motion) parameter and/or biometric parameter. The noise attenuation and/or removal process may be passive or active, using passive and/or active filtering. In one embodiment, the signal extraction processing circuit 710 may comprise a motion processing circuit 712, a biometric processing circuit 714, and a noise processing circuit 716, e.g., as disclosed in FIG. 2 of WO 2013/109390 and FIG. 1 of WO 2013/019494, both of which are incorporated herein by reference, and show additional details regarding signal extraction processing circuit 710. In the illustrated embodiment, a motion processing circuit 712 may be configured to process a motion signal output by the motion sensor(s) 14a and/or a biometric signal output by the biometric sensor(s) 14b. When configured to measure user cadence, the motion processing circuit 712 may comprise the parameter circuit 100. The noise processing circuit 716 may be configured to remove or otherwise attenuate cadence-related motion artifact noise from a biometric signal output by a biometric sensor 14b and/or a biometric parameter output by the biometric processing circuit 714, based, e.g., on the user cadence output by the parameter circuit 100 (e.g., motion processing circuit 712). Stated more broadly, the noise processing circuit 716 may be configured to remove or otherwise attenuate motion information from a biometric signal output by the biometric sensor 14b and/or from a biometric parameter output by the biometric processing circuit 714. For example, a determined cadence frequency may be selectively (actively) removed from the frequency spectrum of the output signals of one or more of the sensors 14 so that higher-quality output signals ("cleaner outputs") are achieved with substantially attenuated motion artifacts. As a specific example, the biometric sensor 14b that outputs the biometric signal may comprise a photoplethysmography (PPG) sensor, where the output biometric signal includes biometric information, e.g., heart rate and respiration rate information, as well as unwanted cadence-related information. The noise processing circuit 716 may process, attenuate, or otherwise remove the unwanted cadence information from the signals output by at least one biometric sensor 14b, generating a cleaner biometric signal. Alternatively or additionally, the noise processing circuit 716 may facilitate selecting the proper value of a biometric parameter that has been estimated by the biometric processing circuit 716. In one example, the noise processing circuit 716 may comprise a signal processing circuit and/or processing method for generating a cleaner biometric signal and/or biometric parameter by attenuating, removing, and/or redacting frequencies associated with a user cadence (such as determined by the motion processing circuit 712). The noise processing circuit 716 may alternatively or additionally incorporate passive filtering, e.g., analog or digital filters that are high-pass, low-pass, notch, bandpass, etc. It will be appreciated that noise processing circuit 716 may also process the motion signal and/or physical activity parameters to generate a cleaner motion signal and/or cleaner physical activity parameters.

Once a cleaner biometric signal and/or cleaner biometric parameter is generated, the cleaner biometric parameter(s) and determined physical activity parameter(s) can be further processed to determine a physiological assessment parameter of the user via an assessment processing circuit (APC) 720. In general, APC 720 determines physiological assessment parameter(s) for a user wearing an activity monitoring device, e.g., ear bud 12, wristband, armband, etc., by processing motion signal(s) to determine a physiological assessment parameter. In one embodiment, APC 720 may process at least one activity parameter and at least one biometric parameter, each determined by the signal extraction processing circuit 710, to determine at least one physiological assessment parameter.

The general principle supporting the physiological assessment methodology implemented by APC 720 is that biometric signals may change in predictable manner due to a change in a user's activity level, and this causal relationship may reflect a personalized biometric model. The APC 720 may be part of the assessment generation system 700 and may employ a personalized biometric model to generate at least one physiological assessment parameter. In a specific embodiment, the APC 720 generates at least one physiological assessment parameter based on a determined user cadence and/or other physical activity parameters, and biometric parameters and/or cleaner biometric parameter(s), and optionally, based on the power $p_m$ of the motion signal. To store measured data and information about the model employed by the APC 720, APC 720 may also have access to memory 170.

As an example of an embodiment of the assessment generation system 700 and associated assessment generation method, the cleaner biometric parameter may comprise multiple biometric parameters, e.g., heart rate (HR), breathing rate (BR), R-R interval, blood oxygen information, etc., such as provided by a PPG or pulse oximetry sensor when used as the biometric sensor 14b. The APC 720 may then generate the physiological assessment parameter(s) by combining the cleaner biometric parameters with the physical activity parameters, e.g., a cleaner cadence.

As a specific example, the assessment processing circuit 720 may determine a start time and a stop time of a significant change in a physical and/or biometric parameter, or the assessment processing circuit 720 may generally identify a significant change in the signals(s) output by the motion sensor 14a and/or the biometric sensor 14b. A ratio may be generated between the biometric parameter and the associated physical activity parameter. The ratio may be an acute, instantaneous ratio, e.g., heart rate divided by cadence, or an average ratio, e.g., average respiration rate divided by average cadence. For example, an average ratio may be generated by averaging multiple biometric parameters over a selected period of time, averaging multiple physical activity parameters, e.g., cadence, over that same period of time, and dividing these average parameters to generate an average ratio. Alternatively, the change in a biometric sensor parameter over a period of time, e.g., caused by a change in the physical activity parameter(s), may be calculated relative to the change in the physical activity parameter(s) over the same period of time to generate a differential ratio, e.g., $(HR_{stop}-HR_{start})/(C_{stop}-C_{start})= \Delta HR/\Delta C$. In either case, the ratios may then be compared with a personalized model to generate a physiological assessment, e.g., of aerobic capacity, e.g., $VO_2$max, $VO_2$, energy expenditure, recovery time, cardiovascular or cardiopulmonary functioning, etc.

For example, two or more users may be compared for physical fitness by comparing their respective $\Delta HR/\Delta C$ ratios. The user having a greater reduction in heart rate with a given reduction in cadence over a fixed period in time may have a greater heart rate recovery rate than a user having a lower reduction in heart rate with the same reduction in cadence over the same time period. Similarly, a ratio for average heart rate $HR_{avg}$ (or other biometric parameter) divided by average cadence $C_{avg}$ can be mapped for a given user over a period of weeks. As the ratio decreases over the course of physical fitness training, the decreasing ratio may be indicative of improving physical fitness. The origin behind this improved cardiovascular (aerobic) fitness level with a decreased average ratio of $(HR_{avg})/(C_{avg})$ is that the decreased ratio indicates that less heart beats are required for the same motion of the user, which may be indicative of a more physically fit cardiovascular system.

However, in some cases, a plurality of users may be moving at the same average cadence but one or more users may be generating less physical power due to a lower strike force during walking, running, cycling, etc. For this reason, a given ratio may be further normalized by the power $p_m$ (or average power $p_{m,avg}$) of the motion signal generated by the motion sensor 14a. For example, for a given user, the average biometric parameter $BS_{avg}$, measured over a period of time, divided by the average cadence $C_{avg}$, measured over the same period of time, may be further normalized by the average power $p_{m,avg}$ over the same period of time to generate a more accurate average ratio that is more closely related to the user's overall fitness level. In this case, the fitness of a user may be inversely proportional to $BS_{avg}/(C_{avg}*p_{m,avg})$, where $p_{m,avg}$ refers to an average motion power of the user over a given time period. It should be noted that this inverse relationship may hold true for many biometric parameters, including but not limited to, HR, BR, blood pressure, 1/R-R, and any other biometric parameters that increase with increasing exercise intensity. This relationship is not likely to hold true for biometric parameters that do not necessarily increase with exercise intensity, and in some cases may actually decrease with exercise intensity, e.g., blood oxygen level. Stated another way, because HR, BR, blood pressure, and 1/R-R generally increase with increasing exercise intensity, while their average values during exercise generally decrease with increased physical fitness, the overall fitness of a user may be inversely proportional to $BS_{avg}/(C_{avg}*p_{m,avg})$. In some cases, the ratio itself may not need to be expressly calculated. For example, by detecting a change in cadence over a period of time via one more elements of system 700, the assessment processing circuit 720 may calculate the recovery rate of a biometric parameter over that period of time, and this recovery rate value may be directly related to a user's overall fitness level. Moreover, the described ratio is not the only mathematical representation that may be used to relate overall fitness with one or more concurrent biometric parameters or physical activity parameters. More generally, the overall fitness with increase with decreasing $BS_{avg}$, and with increasing $C_{avg}$ and $p_{m,avg}$.

Figure 8:
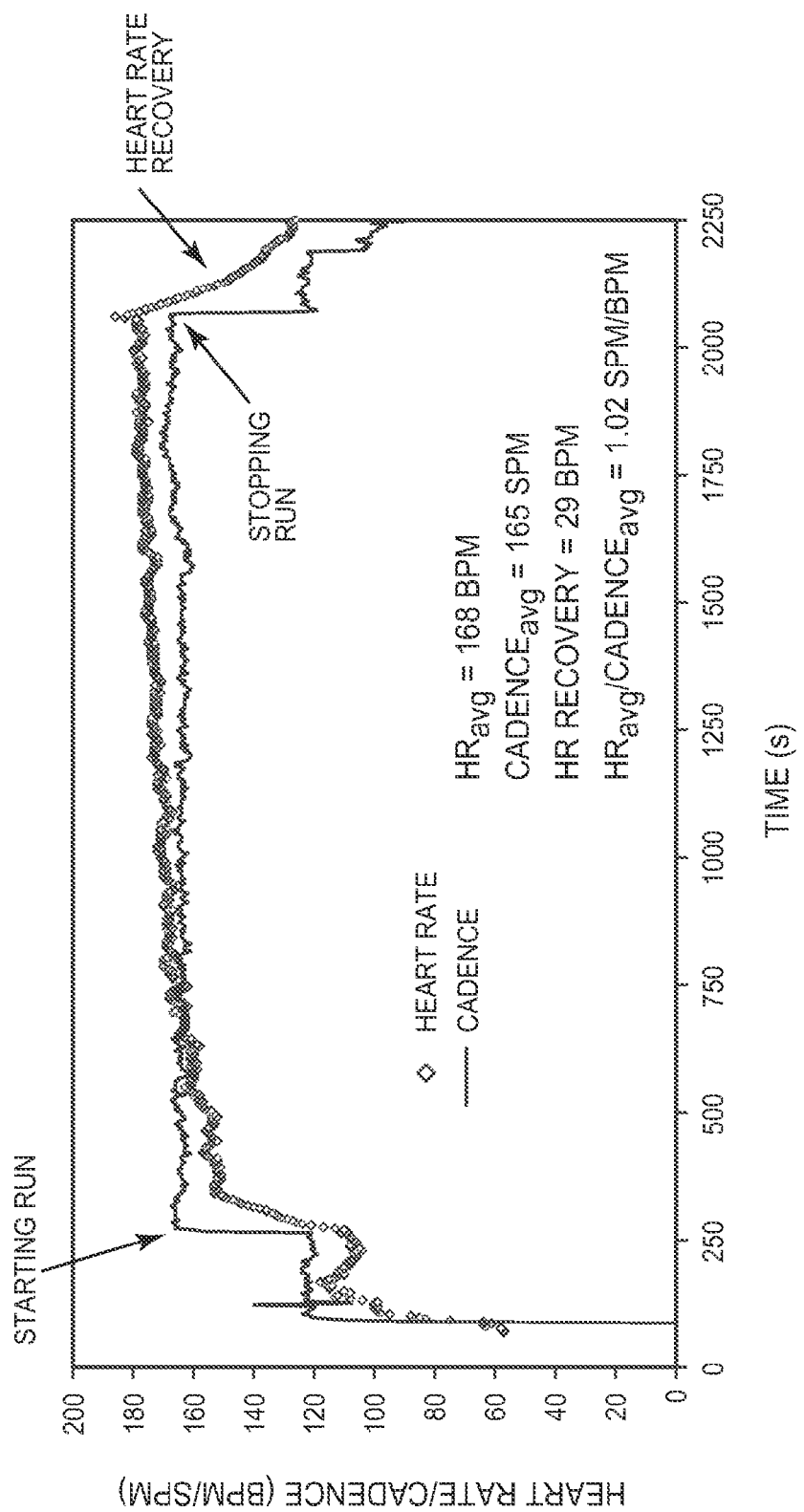
FIG. 8 shows simulation results associated with the assessment system of FIG. 7.

FIG. 8 shows an example of $\Delta HR/\Delta C$ produced by the assessment generation system 700 to determine the fitness level of a user. In this example, the user wore a biometric headset according to the embodiments presented herein, wherein the biometric sensor 14b comprised a PPG sensor in the right earbud of the biometric headset and the motion sensor 14a comprised a MEMS 3-axis accelerometer (also in the right earbud). Examples of such a headset may be found in U.S. Patent Publications 2008/0146890, 2010/0217098, 2010/0217099, 2010/0217102, 2012/0197093, 2013/0131519, and 2014/0012105, all of which are incorporated by reference herein. The processed (cleaner) heart rate measurement vs. time is shown as BPM (beats per minute) and the cadence measurement vs. time is shown as SPM (steps per minute). The assessment processing circuit 720 determines the start and stop times (and thus the period of time) of the analysis by detecting a substantial increase in cadence, e.g., an increase of more than 20 SPM, and by detecting a substantial decrease in cadence, e.g, a decrease of more than 20 SPM. Because the start and stop times can also be determined, various physiological assessment parameters can be determined, e.g., recovery rate. For example, the APC 720 calculates the 1-minute heart rate recovery by recording the measured heart rate at the stopping point, recording the measured heart rate at 1-minute past the stopping point, and subtracting the latter from the former. In this example, the user had a 29 beat decrease over 1 minute, and thus had a $HR_{rec}$=30 BPM. The assessment processing circuit 720 also calculates the average HR ($HR_{avg}$) and average cadence ($C_{avg}$) over the period of time to calculate $H_{avg}/C_{avg}$, which in this example was 1.02. Higher recovery rates and/or lower ratios are generally associated with better health/fitness.

Figure 9:
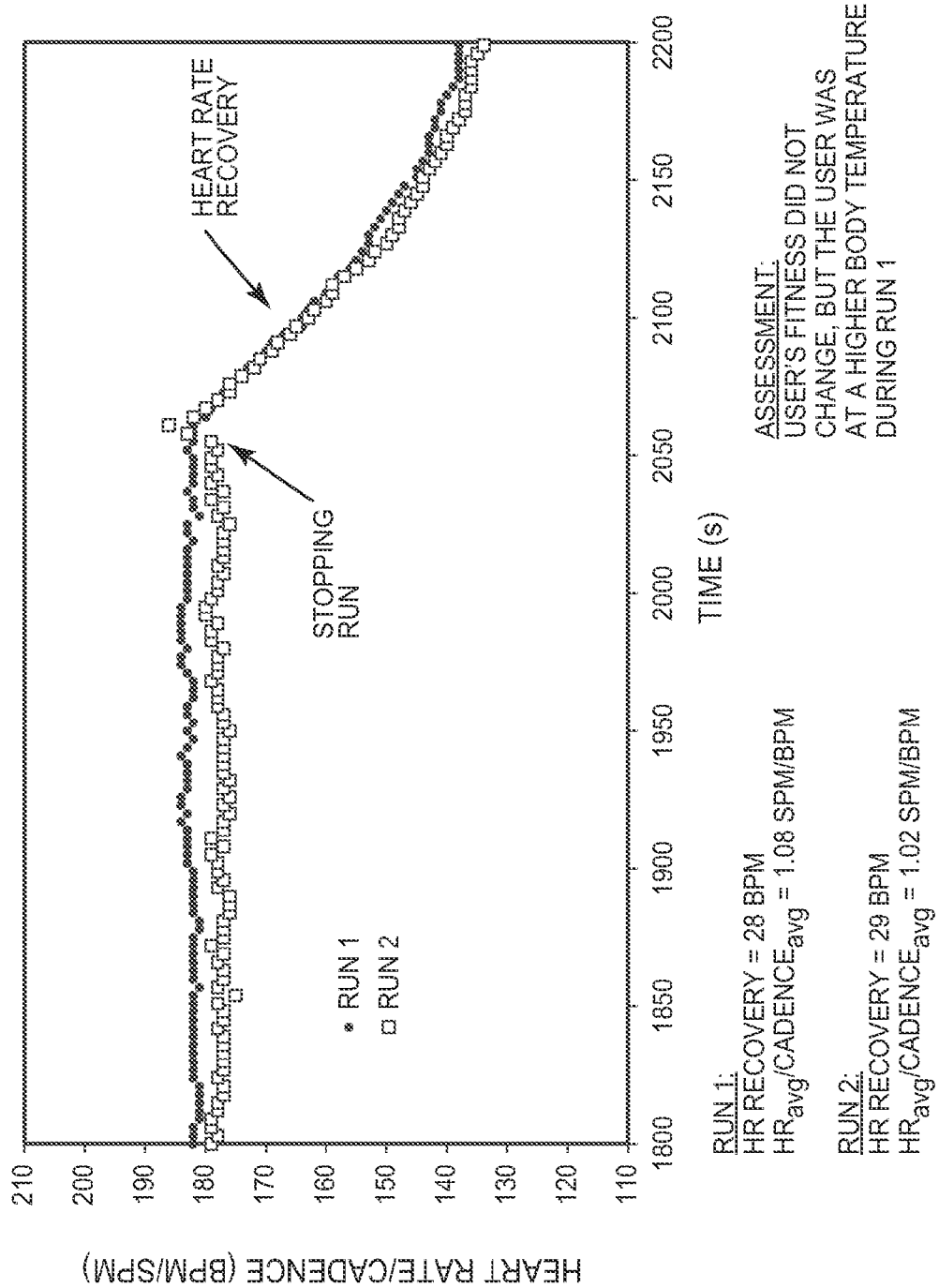
FIG. 9 shows simulation results associated with the assessment system of FIG. 7.

In another example, assessment processing circuit 720 generates a physical assessment parameter for a user based on data from multiple exercise sessions, as shown in FIG. 9. Data from multiple exercise sessions (e.g., runs) enables the assessment processing circuit 720 to make determinations about some parameters, e.g., metabolic rate, without specifically measuring such parameters. In this example, the user wore a biometric earbud, e.g., such as previously described in reference to FIG. 8, where the user ran without a cooling fan during Run 1 and with a cooling fan during Run 2. A cooling fan is often used in treadmill runs to cool-down the skin and help evaporate sweat from the body. In FIG. 9, the measured heart rate vs. time is presented for the two exercise sessions where the user was running at the same speed (6 mph) for the same duration of time (30 minutes). For the sake of simplicity, the cadence vs. time for each run is not shown. The assessment processing circuit 720 identified the stopping point of the two runs by the dramatic drop in cadence of more than 20 SPM (signified by the dotted line). The assessment processing circuit 720 also measured the HR recovery rates and the average ratios ($HR_{avg}/C_{avg}$) for each run, as shown in FIG. 9. Because the user's HR recovery rate did not significantly change from run to run, while the user's average ratio did change significantly, the assessment processing circuit 720 determined that the user was exercising at a higher body temperature during Run 1 than during Run 2. The theory supporting this determination is that HR recovery is more related to cardiac output, where the higher the heart rate recovery, the higher the cardiac output, and the greater the overall physical fitness (cardiovascular fitness). However, the average ratio ($HR_{avg}/C_{avg}$) is more closely related to overall acute (or current) stress on the heart muscle, which increases with body temperature. The average ratio $HR_{avg}/C_{avg}$ may also be related to the overall physical fitness of the user, but because the APC 720 is able to calculate essentially the same HR recovery rate for Run 1 and Run 2, the assessment processor is able to determine that the origin of the higher average ratio for Run 1 was due to a higher user running temperature.

The personalized model used by the assessment processing circuit 720 may comprise an a priori model of a known relationship, a calibrated model, or a model generated over time based on a previously unknown relationship using a history of the collected data. For example, the physiological assessment parameters determined based on the Run 1 and Run 2 data shown in FIG. 9 were determined using an a priori model. In contrast, a calibrated model may compare one or more of the aforementioned ratios (the estimated value) to the results of a standard ("benchmark") fitness test (the actual value), e.g., a heart rate recovery test, $VO_2$max test, submax test (such as a Rockport Test), or the like. A calibration factor, relating the estimated versus actual value of the physiological assessment may then be generated for future use in predicting the physiological assessment using the calibration factor multiplied by the ratio. For example, the physiological assessment parameters shown in FIG. 9 can be tested against a benchmark test of $VO_2max_{actual}$, and the resulting relationships between the $HR_{avg}/C_{avg}$ and $VO_2max_{actual}$ and/or HR Recovery and $VO_2max_{actual}$ can be stored in memory 170 for future estimations of $VO_2max_{estimated}$. As a specific example of a calibrated model, consider FIG. 10, which plots the Measured $VO_2$max (measured via gas-exchange analysis) of three users vs. a measured relationship, e.g., a slope of $HR_{recovery}$ vs. $HR_{response}$. Namely, the HR and C of each user was measured with a PPG-based biometric armband sensor having the same biometric- and activity-monitoring functionality as the biometric earbud shown in FIG. 8. In this testing, however, data was collected for each user during everyday living conditions (free living), as opposed to a treadmill run, and periods of physical activity were defined as a user having an elevated cadence, e.g., a cadence higher than 100 steps/min, for a certain period of time. For each of the users, the APC 720 was configured to identify targeted time periods, defined by an active time period having at least 10 seconds of physical activity followed by a rest period having at least 20 seconds of rest. For each targeted time period, the APC 720 generates a linear relationship between the drop in heart rate over the rest period ($HR_{recovery}$) vs. the rise in heart rate over the active period ($HR_{response}$), and generates a characteristic slope for this relationship. In one embodiment, this characteristic slope is generated by plotting, for each targeted time period, all measured $HR_{recovery}$ values vs. all measured $HR_{response}$ values and generating an average slope for this relationship, such that this average slope is the characteristic slope. Because the measured $VO_2$max of each user was measured in advance and stored in memory 170, the characteristic slope may be calibrated against the measured $VO_2$max with the linear relationship shown in FIG. 10. This yielded a calibrated estimate of $VO_2$max based on the slope relating $HR_{recovery}$ to $HR_{rise}$.

Figure 10:
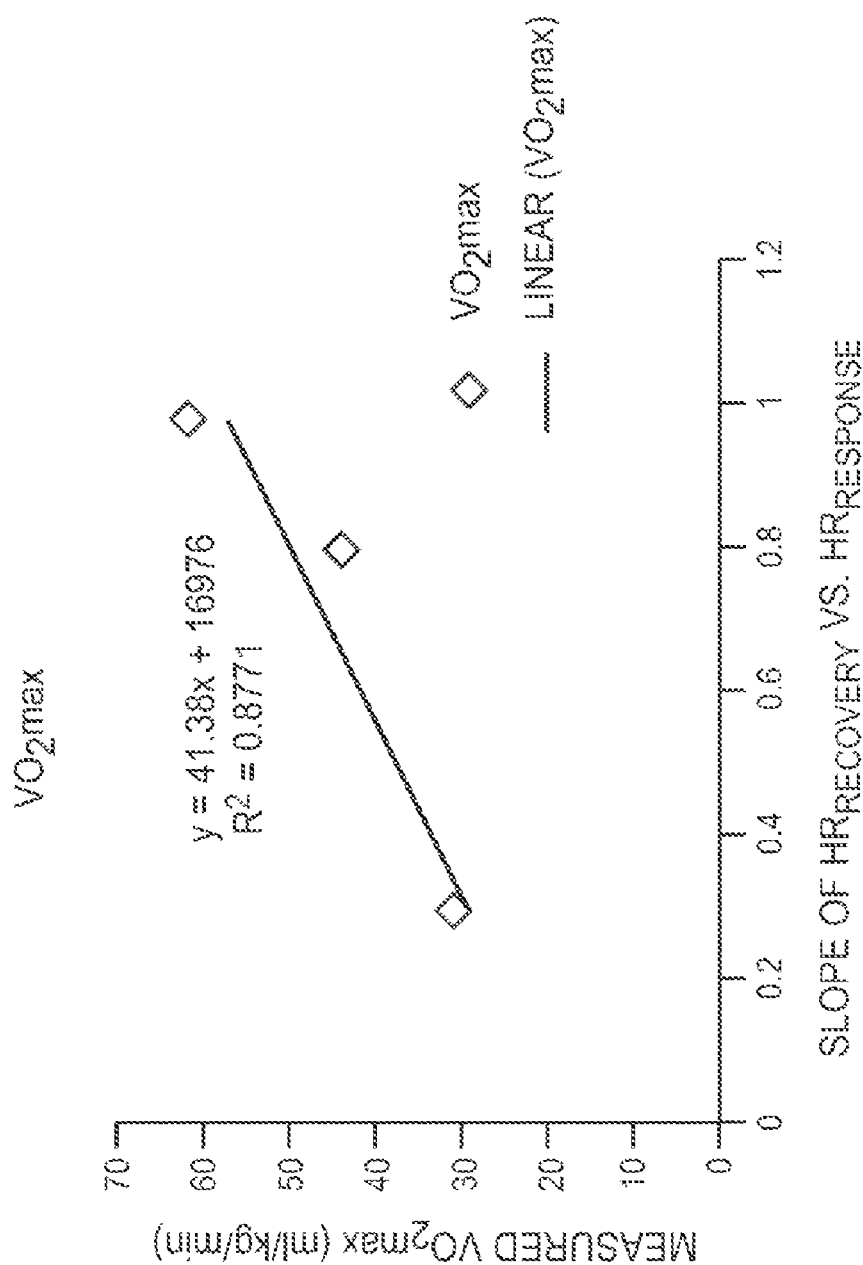
FIG. 10 shows simulation results associated with the assessment system of FIG. 7.
Figure 11:
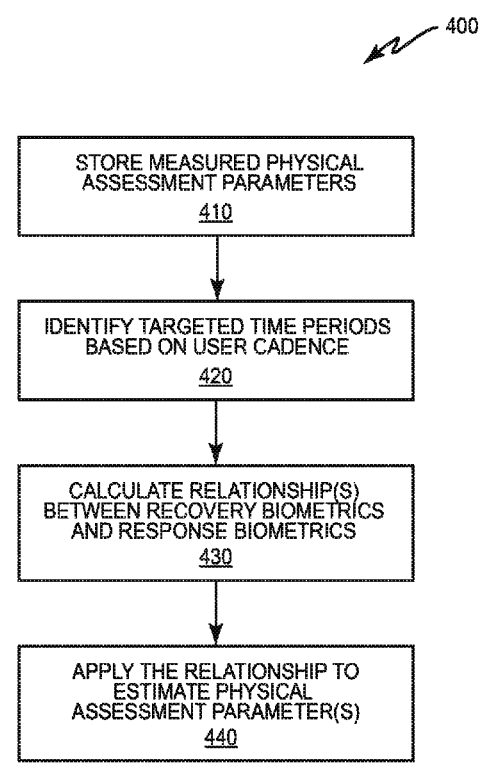
FIG. 11 shows an exemplary process for obtaining the simulation results of FIG. 10.

FIG. 11 outlines a general method 400 for producing the results of FIG. 10. Measured physiological assessment parameters are stored in memory 170 (block 410). APC 720 identifies targeted time periods based on the user cadence (block 420), e.g., by identifying active and rest periods as indicated above. Subsequently, the APC 720 determines the relationship(s) between the recovery and response biometric parameters, e.g., $HR_{recovery}$ and $HR_{rise}$ (block 430). The APC 720 may additionally map the relationship(s) with the stored physiological assessment parameter such that the relationship(s) may then be used at any later times to estimate future physiological assessment parameters without actually having to measure such physiological assessment parameters (block 440).

An example of a third type of model, e.g., the model generated over time based on a learned relationship, is a model relating diet to overall physical fitness. For example, a user recording their diet over several weeks and exercising with system 700 will generate numerous datasets that may be used by the APC 720 to generate physiological assessment parameters. If the user keeps track of their food intake with a digital food diary that is accessible to the APC 720, the APC 720 may also correlate food intake over time with the aforementioned fitness assessments (e.g., HR recovery, average ratio, $VO_2$max, etc.) to generate a correlation between at least one food constituent and one of the fitness assessments. In this manner, an individual can generate a personalized map of foods associated with higher or lower fitness for that individual. The greater the granularity of ingredients recorded by the food diary, the more specific the correlation may be between fitness level and diet. Examples of potential food constituents include, but are not limited to: calories, carbohydrates, fats, proteins, vitamins, minerals, sugars, and electrolyte (sodium, potassium, etc.) levels. Furthermore, further granularity may be provided by the types of these different constituents, such as the type of protein, vitamin, or salt, for example. Moreover, by combining the user's food diary information with biometric sensor readings from mastication or swallowing (as described below), the APC 720 may generate a confidence indicator for the users manual input into the food diary. Using this technique, it may be more challenging for the user to "fool" the APC 720 as it calculates the correlation between diet and fitness.

In one embodiment, one or more elements of the system 10 may also identify the context of the user's activity, e.g., a lower activity state, by e.g., identifying a time period of substantially lower cadence and/or substantially lower power $p_m$. The time period associated with the context determination may be the same as, different from, or overlap any other assessment time periods. This identification may in turn change the contextual framework used by the APC 720. The APC 720 may then process the cleaner biometric parameter(s) differently than during a time period, e.g., a targeted time period, where cadence and/or power is determined to be substantially higher, e.g., when there is a higher activity state, such as a higher average cadence and/or motion power. For example, a change in the biometric parameter over a given time, in the context of a lower activity state, may be indicative of a classifiable biometric event. For example, a change in heart rate of 1-15 BPM over 15-40 seconds may be associated with a swallowing event. In such case, the APC 720 may classify and count the number of swallowing events over a period of time and generate an estimate for the duration of mastication. In contrast, if system 10 identifies a higher activity state, the APC 720 may be redirected away from classifying and counting swallowing events and towards identifying a physical fitness level, e.g., using the aforementioned method. In this manner, the determination of a user's activity level can be used to change the context of the processing executed by APC 720, and thus change the methodology executed by the APC 720.

In some cases, the determined contextual framework can be used by the APC 720 to change the "polling" (the electrical biasing and/or sampling) of the sensor(s) 14*a* and/or 14*b*. For example, the determined cadence or motion power may be processed to change one or more sensor operating parameters, e.g., the voltage, current, duty cycle, bias frequency or phase, bias waveform, biasing period, sampling time, sampling integration period, sampling routine, etc., of an optical emitter and/or detector in a PPG sensor embedded in a wearable device (such as the earbud of FIG. 1). Such processing may be beneficial for saving battery power in the wearable device, as it may not be advantageous to continually bias a sensor when no useful biometric information is anticipated. As a specific example, consider the heart rate vs. time plots of FIG. 8 and FIG. 9. The average heart rate can be effectively estimated during most of the run using just a few heart rate data points. However, many more data points are required to accurately trace the rise time and fall time of the heart rate during the beginning and end of the run. In this example, APC 720 can be configured to detect a rapid change in cadence and then initiate a control signal to the sensor to increase the polling (such as an increased bias frequency or period) to collect higher-acuity data during the period of time where the heart rate is most likely to substantially change. The sampling rate may also increase. Alternatively, the sensor polling may normally be set to a high polling, and when APC 720 detects a steady cadence and/or steady heart rate, the APC 720 may then send a signal to lower the sensor polling. The time period for changing the sensor operating parameter(s) may be arbitrarily set in advance, based on an a priori model, e.g., by setting the period from 10 seconds to 10 minutes, or may be determined uniquely for the user over a period of time. After the time period for changing the sensor operating parameter(s), the sensor operating parameter(s) may then return to the previous level (or some predefined default level). Though a specific example has been given for a PPG sensor, this variation also applies more broadly to any sensor in a wearable device, e.g., an electrically biased sensor.

Figure 12:
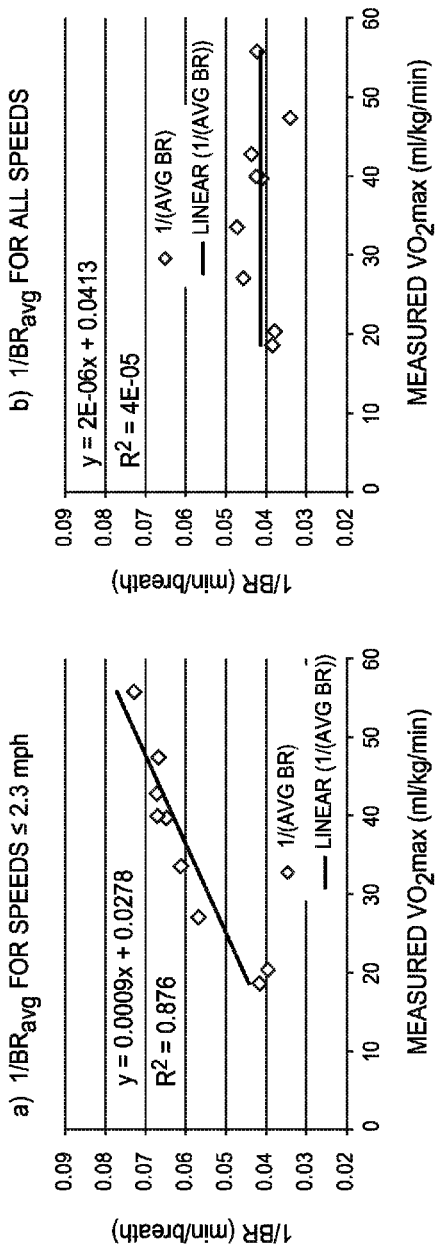
FIGS. 12a and 12b show simulation results associated with the assessment system of FIG. 7.

Another example of using a contextual framework for a physiological assessment is shown in FIG. 12, which presents the average breathing rate ($BR_{avg}$) for a group of nine female users under two different contextual frameworks, where different diamonds in FIG. 12 indicate different users. Each user had previously been evaluated via gas-exchange analysis to generate an objective (benchmark) measurement of their $VO_2$max (measured $VO_2$max). These users were each monitored throughout a variable treadmill run via a biometric headset (e.g., as described earlier), with average speeds ranging from 2.46 mph to 4.4. mph. Each biometric headset was measuring heart rate, breathing rate, cadence, and other parameters in real time for each user as each user was running. Using the methodology described herein, each user's speed was calculated in real time by a processor, e.g., the signal extraction processor 710 and/or APC 720, factoring user cadence, stride length, and other parameters. During this time, the APC 720, for each headset, calculated the average breathing rate for the user and the estimated $VO_2$max of each user via a formula directly relating $1/BR_{avg}$ to measured $VO_2$max. The formulas are shown in FIGS. 12*a* and 12*b*. FIG. 12*b* shows the relationship between each of the nine users when the breathing rate was averaged over each speed, with a contextual framework that does not discriminate between speeds. Note there is a not a significant relationship ($R^2$=0.186) between $1/BR_{avg}$ and measured $VO_2$max when the contextual framework does not discriminate for a particular range of speeds. In contrast, FIG. 12*a* shows the relationship between each of the nine users when the breathing rate was averaged only over a period of time where the average user speed was ~2.3 mph. For this contextual framework, there is a strong relationship ($R^2$=0.876) between $1/BR_{avg}$ and measured $VO_2$max. Thus, the APC 720 can be used to identify the user's speed (via user cadence and other parameters) and selectively average the breathing rate only for a time period where an average speed of 2.3 mph or less is identified. The end result is an accurate estimate of the users $VO_2$max factoring solely $1/BR_{avg}$. Note that the user's weight, height, and other parameters are not factored into this model of estimated $1/BR_{avg}$ vs. estimated $VO_2$max, which exemplifies the robustness and utility of this model.

Figure 13:
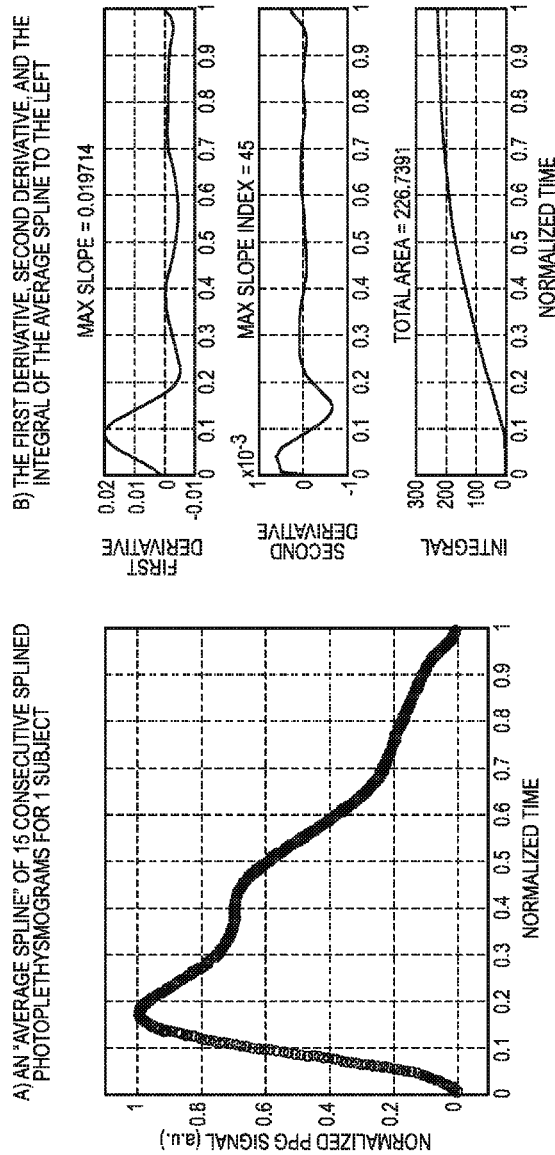
FIGS. 13a and 13b show exemplary details associated with generating a model used by the assessment system of FIG. 7.
Figure 16:
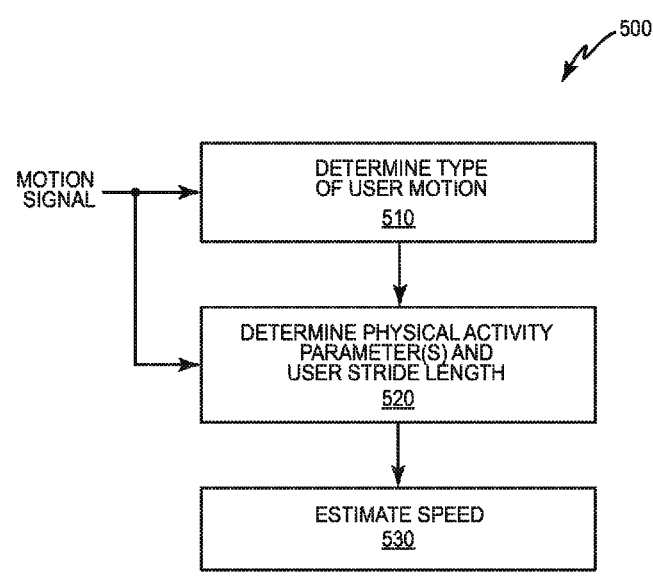
FIG. 16 shows an exemplary process for estimating a user speed.

FIG. 13 shows another example of a model generated over time based on a learned relationship via data pre-processing (data parameterization) and machine learning. The "learned model" in this case is a learned relationship between measured blood pressure (as measured via a blood pressure cuff) and the PPG signal (as output from a biometric earbud, e.g., shown in FIG. 8). In this particular study, the PPG sensor 14*b* was configured to detect blood flow changes from the ear region, between the anti-tragus and concha of the ear, e.g., as described in U.S. Pat. No. 8,647,270 and U.S. Pat. No. 8,700,111. For this model, several users were studied wearing a biometric sensor while also wearing a blood pressure cuff to measure blood pressure. In this study, however, the APC 720 was configured to execute the following:

1) Determine whether the user cadence was below a threshold (~100 steps/minute) in order to assure data integrity of the PPG signal.

2) If so, high-pass filter the PPG signal to remove (or attenuate) DC and low-frequency components.

3) Buffer numerous pulses of data (e.g., at least ten complete signals) and identify the beginning and end points of each signal in the time domain.

4) Create a spline for each signal across a finer mesh of constant size—in this case 500 samples—so that the signals are effectively normalized in time to eliminate pulse rate dependence.

5) Average the splines to produce a single "average spline" signal representing the average pulse shape.

6) Normalize the amplitude of the average spline signal—normalized between 0 and 1—across a time axis of 500 points for one wave period (e.g., normalizing and discretizing over 500 points). While this particular study used 500 points, later studies have shown that a 4× decimation of data points did not degrade blood pressure model accuracy. This suggests that 125 points, and perhaps even fewer points, may be sufficient to maintain model accuracy.

7) Differentiate and integrate the average spline signal to provide multiple representations of the data to the machine learning tool.

The data resulting from this processing as executed by the APC 720 was then analyzed outside of the APC 720 using a machine learning tool. The resulting model was later added to the APC 720 "tool box" to enable the generation of a blood pressure assessment. To summarize the machine learning methodology, seventy-two datasets were available for the machine learning tool, with data comprising both raw PPG data from the biometric sensor and measured blood pressure data from a standard blood pressure cuff. The mean values for systolic BP, diastolic BP, and pulse pressure were 129.0±9.3, 83.6±8.0, and 45.5±9.0 mmHg, respectively with a mean heart rate of 73.8±9.4 BPM. These datasets were divided into 48 sets for model development and 24 sets for model validation. The neural network consisted of a set of inputs (the input layer), a set of outputs (the output layer), and a set of hidden layers. Three networks were built, each with multiple input nodes (FIG. 14) and a single node output layer: systolic pressure, diastolic pressure, or pulse pressure. The input layer consisted of a set from the available waveform representations shown in FIG. 13. The representations (each normalized and discretized as described earlier) were called (i) "wave" for the normalized PPG signal, (ii) "first derivative", (iii) "second derivative", and (iv) integral. Each representation was used individually, as well as in combination with other representations. The data was explored by running many trials with various combinations of the available input datasets paired with a given output layer. Experiments examined different hidden layer topologies and learning strategies. Once an optimized model was developed for the training dataset by the machine learning tool, the model was applied to the validation dataset, and a summary of the results of the model is presented in FIG. 15. In FIG. 15, the closer a particular value is to "1," the better that waveform is at predicting the corresponding parameter. The optimized model itself is embodied by a myriad of coefficients that relate inputs to outputs; the number of coefficients in the resulting model was ~7800 for systolic pressure, ~15,700 for diastolic pressure, and ~23,000 for pulse pressure (FIG. 14).

Of interesting note, the best representation (defined by the best correlation coefficient for the model against the validation data) for each output layer type was different. To predict systolic blood pressure, e.g., the wave (e.g., the pulse wave, also known as the PPG waveform) provided a better correlation than any other individual representation. However, the "wave" was the poorest predictor of diastolic blood pressure, the integral representation provided the best correlation for predicting diastolic blood pressure, and the first derivative provided the best predictor for pulse pressure. In principle, the models of FIG. 14 are "single representation" models, as they employ coefficients relating to a single transform only (e.g., integrals only, pulse waves only, first derivatives only, etc.). However, additional models were explored, factoring the "best of two" transforms. The last column of FIG. 15 shows the results. In the case of systolic and diastolic pressure, e.g., slightly better correlational coefficients were observed by factoring the best two transforms. For example, input nodes comprising both the second derivative and integral of the PPG waveform resulted in a better correlation for the diastolic pressure than did the integral alone. The resulting optimized model was then incorporated into the APC 720. It should be noted that an assessment of user cadence was critical for autonomous operation of this blood pressure (BP) assessment method, as the method is sensitive to the shape of the PPG signal. It should further be noted that other parameterizations of the PPG signal may be used with this solution, e.g., higher-order derivatives (3rd, 4th, etc.), higher-order time-integrals, spectral representations of the signal(s), spectral representations of the derivatives or integrals of the signal(s), and the like. It should also be noted that although the experiment behind FIGS. 13 and 15 was based on PPG measurements from the ear, the embodiments disclosed herein are not limited to this region of the body and, rather, translates to any region of the body where sufficient blood flow modulations can be measured, e.g., the wrist, arm, leg, digits (e.g., fingers and/or toes), nose, head (e.g., forehead, face, temple, ear region, etc.), neck, torso, and other regions of the body. However, the choice of location of the PPG sensor 14b may change the shape of the collected PPG waveform, and thus, the coefficients relating the biometric parameters (e.g., the "pulse wave" shape, "first derivative," "second derivative," and integral of the normalized PPG signal) to blood pressure may be different. For this reason, it is generally recommended that the circuit, e.g., the APC 720, be retrained each time the PPG sensor 14b is place on a different body part or each time the PPG optomechanics are changed. Lastly, while the experiment behind FIGS. 13 and 15 resulted in mathematical relationships applying broadly to multiple individuals, the same solution may be applied towards a single individual, with "training" datasets feeding into the machine learning tool that are associated with one person only (and not a group of persons). In such cases, the accuracy of the resulting blood pressure model may be higher for a single individual. However, the resulting "individual" algorithm may not be scalable to a broad population of subjects, and the APC 720 may need to be recalibrated (against a known blood pressure benchmark, e.g., as provided by a conventional blood pressure cuff) for each user wearing the device.

The previous discussions focused on determining various physiological assessment parameters based on biometric and motion signals. In another embodiment, the speed of a user may be estimated based on the motion signal output by a motion sensor disposed proximate the user. In this embodiment, the estimated speed is determined using an estimated stride length (as opposed to an actual measurement of the stride length) of the user. FIG. 15 shows one exemplary process 500 implemented by the APC 720 to estimate the user's speed. The APC 720 processes a motion signal output by the motion sensor to determine a type of motion (block 510). Exemplary types of motion include but are not limited to, resting, walking, running, and sprinting. APC 720 then processes the motion signal based on the determined type of user motion to determine one or more physical activity parameters and to estimate a stride length of the user (block 520). Subsequently, the APC 720 estimates the speed of the user based on the determined physical activity parameter and stride length (block 530).

In one exemplary embodiment, the physical activity parameter(s) include the user cadence when the type of motion is walking or running. For example, the APC 720 estimates the speed based on a user cadence and the estimated stride length when the user is walking or running. In another embodiment, APC 720 determines the stride length (used to estimate the speed) based on a user cadence and at least one non-cadence activity parameter when the type of motion comprises a running motion. When the type of motion comprises a walking motion, the APC 720 determines the stride length based on the user cadence and at least two non-cadence activity parameters. For example, if the identified type of motion is running or walking, APC 720 determines they user speed (e.g., in meters/minute) according to:

$$C1*SL*C, \quad (4)$$

where C represents the running or walking cadence, SL represents the estimated stride length, and C1=1 when the speed is given in meters/minute. For this example, a running stride length $SL_R$ may be calculated according to:

$$SL_R = C2 + C3 * C_R * AP1, \quad (5)$$

when the identified type of motion is a running motion, where $C_R$ represents the running cadence, C2 and C3 represent experimentally derived constants, and AP1 represents a physical activity parameter or parameterization. Alternatively, a walking stride length $SL_W$ may be calculated according to:

$$SL_W = C4 + C5*AP1 + C6*AP2 + C7*C_W*AP1 + C8*C_W*AP2, \quad (6)$$

when the identified type of motion is a walking motion, where $C_W$ represents the walking cadence, C4 through C8 represent experimentally derived constants, AP1 represents a physical activity parameter or parameterization, and AP2 represents an additional physical activity parameter or parameterization. The values of the experimentally derived constants will depend strongly on the type of motion sensor used to generate the cadence. For example, when the motion sensor is an accelerometer, the constants may depend on the type of accelerometer used. These constants can be generated by measuring the actual stride length of the user or group of users with a ruler, collecting the accelerometer outputs, and solving for the aforementioned equations empirically for a known cadence, predetermined AP1, and predetermined AP2. The physiological reasoning behind a more complicated formula (requiring multiple physical activity parameters or parameterizations) for stride length during walking (versus running) may be explained by the fact that running comprises a more uniform acceleration pattern for a broad user group when compared with walking, which is characterized by more individual variation. Namely, the accelerometer outputs for running are more similar for a mass population than the accelerometer outputs for walking in a mass population. Stated another way, there are more ways to successfully walk than there are to successfully run, and the accelerometer outputs for walking contain motion information due to a variety of body motions (not necessarily associated with cadence) that are not typically seen during running. Additional improvements in the stride length estimation may be generated by adding additional parameterizations of the activity (such as additional parameterizations of an accelerometer output signal), e.g., adding AP3, AP4, AP5, etc.

For the case of measuring user speed during cycling, stride length may not be relevant. And the circumference of the bicycle tires may also not be very useful without context of the gear setting. Thus, to measure speed during cycling, the APC 720 may first determine that the user is cycling (using methods described earlier). Then the APC 720 may define the measured cadence as a cycling cadence. The acceleration may also be measured by an accelerometer 14*a*, which may also be providing the motion signal for processing the cadence. With the cycling cadence and acceleration known, the APC 720 may then estimate the speed of the user during cycling. This estimation may comprise a look-up table for mapping cadence and/or acceleration values with user speed. APC 720 may also estimate user speed by estimating the gear setting required for a given cadence and acceleration value. Other estimation methods may be employed for speed as a function of user cadence and/or acceleration. Alternatively, the APC 720 may not estimate speed but may rather generate a dimensionless value that is a function of user cadence and acceleration and then send this dimensionless value to a remote device (e.g., a smartphone, sport computer, cycling computer, smartwatch, etc.) for estimating speed via algorithms (e.g., calibration algorithms) on the remote device.

Figure 17:
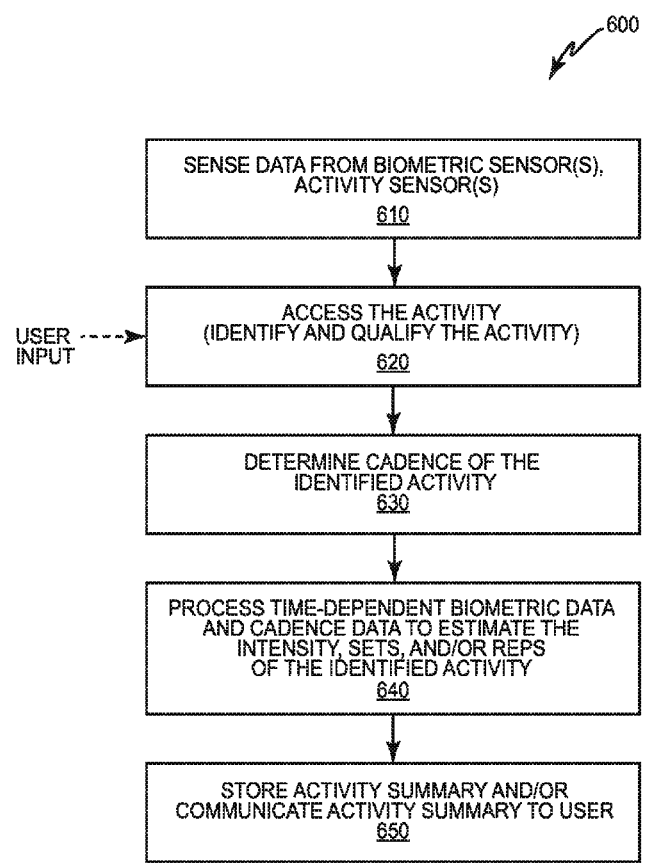
FIG. 17 shows an exemplary process for generating personalized activity summaries.
Figure 18:
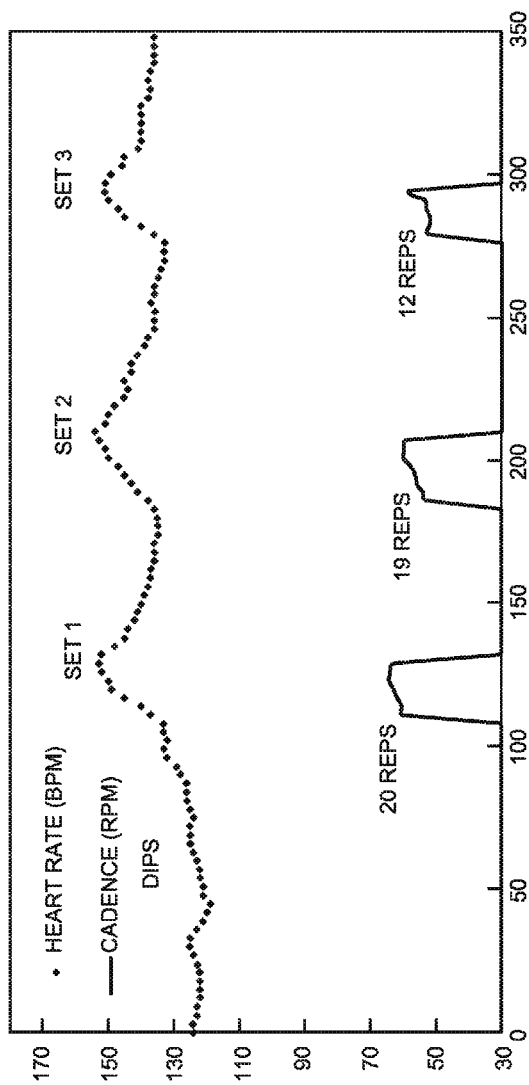
FIG. 18 shows simulation results associated with the process of FIG. 17.

The assessment generation system 700 of FIG. 7 may also be used to generate personalized activity summaries based on user biometric data and user cadence. FIG. 17 shows an exemplary method 600 for generating such personalized activity summaries. After sensing data from at least one biometric sensor 14*b* and at least one motion sensor 14*a* and processing the sensed data to generate at least one activity parameter and at least one biometric parameter (block 610), the system 700 assesses the activity to identify and/or quantify the activity (block 620). The system 700 then determines the cadence of the identified activity (block 630). In one exemplary embodiment, the APC 720 may process the physical activity parameter of the peak motion frequency and determine the cadence of the activity based on some multiple of the peak frequency that correlates best with the identified activity. The system may then process biometric data (e.g., one or more biometric parameters) and cadence data over a period of time to estimate the intensity of the activity, (block 640), and store and/or communicate a summary of the activity (block 650). FIG. 18 shows data from a real-life example of this system 700 in action. In particular, FIG. 18 shows a graph of actions/minute (e.g., a heart rate beats per minute and a cadence) vs. time (in minutes) for a user wearing a PPG-based heart rate monitor at the ear. In the example of FIG. 18, the user was performing "dips" (a triceps exercise). By processing sensor readings from the sensors 14*a*, 14*b*, the system 700 was able to generate time-dependent heart rate and activity information. In this particular example, the APC 720 identified that the activity was not jogging or cycling, e.g., by using threshold comparisons (as described earlier), and so the APC 720 interpreted the time-dependent accelerometer signals as a cadence of exercise repetitions, e.g, "dip" repetitions, and not footsteps. This distinction is important, as the peak frequency of the motion signal associated with a repetition exercise may be a multiple of the actual cadence, depending on how the motion signal is processed, and in some cases the cadence may be a multiple of the peak frequency of the motion signal. For example, if the compression and relaxation cycles generate similar motion signals, then the peak frequency of the motion signal may be twice that of the actual exercise cadence. In this case, the system 700 divides the peak frequency by two to determine the true cadence. After identifying the true cadence of the activity, the data may be stored and/or presented to the user, e.g., via a visual display (as shown in FIG. 18). Further, by counting the number of peaks in the heart rate signal, the APC 720 is able to determine the number of sets (the number of times the user began a period of repetitions). In the example of FIG. 18, there are three peaks in the heart rate signal, and thus the user did three sets. Also, the APC 720 may determine the number of repetitions by, e.g., integrating the time-dependent cadence reading over time. It should also be noted that the intensity of each set (in terms of user energy expenditure per set) may be approximated by factoring the heart rate, cadence, and/or a function of the heart rate and cadence for each set. One exemplary method determines the intensity of each set by integrating the heart rate and the step rate over time, and multiplying the products of these two integrals for each set. Another exemplary method combines these two integrals into a regression equation, where each integral is multiplied by a coefficient and the products are summed together and correlated with an intensity benchmark sensor (e.g., gas-exchange analysis used in an indirect calorimeter).

A few important points should be mentioned about the method 600 of FIG. 17. First, the method may optionally employ user input regarding the physical activity performed. The system 700 may use this user input to directly determine the activity being performed by the user, or to facilitate the determination of the activity being performed (block 620). As noted herein, the user input is not required, but it may improve the accuracy of the activity interpretation, and thus may improve the accuracy of the cadence determination since the appropriate motion frequency-to-cadence multiplier (e.g., ½×, 1×, ³⁄₂×, 2×, etc.) may be determined, as previously described. For example, there may be a user interface (audible, touch-based, visual, etc.) for the user to communicate the type of activity being performed. In a specific example, the user may vocalize the activity being performed via a smart device, e.g., an audio headset (as in the particular example of FIG. 18, where the audio headset and sensor(s) 14 are integrated together) or a mobile or fixed remote device (e.g., a wearable computer, digital music player, mobile phone, router, cloud server, camera, etc.), that is in wired or wireless communication with the wearable sensor(s) 14. The smart device may comprise voice recognition algorithms for processing vocal information and interpreting that the user is beginning to perform an exercise. Similarly, the user may input the activity information into a mobile device via a touchscreen or the like.

Second, although the described method 600 was exemplified with an earbud used as the sensor housing form-factor, the described embodiments broadly apply to any wearable form-factor (e.g., wristbands, armbands, leg bands, rings, jewelry, clothing, headbands, patches, smart tattoos, etc.) that comprise a biometric sensor 14b and a motion sensor 14a (though the embodiments described herein are especially suited for any sensor employing both PPG and accelerometry). The key difference with different form-factors is that the peak motion frequency-to-cadence conversion ratio may be different depending on the location on the body where the user is wearing the device, as different harmonics may be introduced into the motion signal depending on the location of the motion sensor 14a on the body.

Third, the processing steps may be performed by the processing circuit 710, the APC 720, or a combination of both (e.g., via distributed processing). In the particular example of FIG. 18, the system 700 was set in a "running" mode," such that the peak frequency was originally assumed to be a running cadence. The processing circuit 710 on the PPG earbud generated the heart rate and "running cadence" information, but the APC 720 determined the physical activity type (e.g., dips) via processing the signal output by the motion sensor 14a, and then applied the appropriate multiplier to the "running cadence" frequency (e.g., the peak motion frequency) in order to determine the correct exercise cadence, e.g., the dips cadence. However, in some embodiments, the processing step for determining a cadence value may follow the processing step for determining the activity type. Also, in some embodiments, either the processing circuit 710 or the APC 720 may execute the entire method 600 alone, without distributing the processing steps.

Various elements disclosed herein are described as some kind of circuit, e.g., a parameter circuit, peak frequency circuit, frequency comparison circuit, cadence processor circuit, power circuit, power comparison circuit, user input circuit, threshold processor circuit, motion processing circuit, biometric processing circuit, noise processing circuit, assessment processing circuit, etc. Each of these circuits may be embodied in hardware and/or in software (including firmware, resident software, microcode, etc.) executed on a controller or processor, including an application specific integrated circuit (ASIC). Further, while the figures show these circuits as being separate circuits operating in communication with each other, one or more of the circuits, e.g., the motion processing circuit, biometric processing, circuit, and noise processing circuit, may be implemented on a single circuit, e.g., a single microprocessor circuit.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. An assessment generation system configured to assess a fitness level of a subject, the system comprising one or more processing circuits configured to:
   measure an average heart rate of the subject with a heart rate sensor worn by the subject over a period of time;
   measure an average cadence of the subject with a cadence sensor worn by the subject over the period of time; and
   calculate a ratio of the average heart rate to the average cadence with a processor operatively coupled to the heart rate sensor and the cadence sensor;
   wherein the one or more processing circuits are further configured to determine a relative body temperature using the calculated ratio of the average heart rate to the average cadence, wherein the higher the calculated ratio the higher the relative body temperature.

2. The assessment generation system of claim 1 wherein the fitness level is inversely proportional to the ratio of the average heart rate to the average cadence.

3. An assessment generation system configured to evaluate an exercise activity comprising one or more sets of exercise repetitions performed by a user via at least one biometric sensor and at least one motion sensor comprised in a wearable monitoring device, the assessment generation system comprising:
   one or more processing circuits configured to:
      process a motion signal output by the at least one motion sensor and a biometric signal output by the at least one biometric sensor to identify a type of the exercise activity;
      process the motion signal using the identified exercise activity to determine an exercise cadence;
      process the biometric signal using the identified exercise activity to determine at least one biometric parameter;
   wherein the one or more processing circuits are further configured to estimate at least one of:
      a number of repetitions of the identified exercise activity using an integral of the exercise cadence; and
      a number of sets of the identified exercise activity using a time-dependent change of the at least one biometric parameter.

4. The assessment generation system of claim 3 wherein the one or more processing circuits are further configured to estimate an intensity of the identified exercise activity using the integral of the exercise cadence and an integral of the at least one biometric parameter.

5. An assessment generation system configured to determine a blood pressure characteristic of a user using a device comprising a photoplethysmography sensor and a motion sensor, wherein the photoplethysmography sensor is proximal to at least some skin of the user, the assessment generation system comprising one or more processing circuits configured to:
   screen data from the motion sensor to determine an integrity of data from the photoplethysmography sensor;
   buffer a plurality of pulses, at least some of the buffered pulses having integrity;
   generate an average pulse shape using the buffered plurality of pulses; and
   determine the blood pressure characteristic using a waveform representation of the average pulse shape.

6. The assessment generation system of claim 5 wherein the one or more processing circuits screen the data from the motion sensor by determining whether a user cadence is below a threshold to determine the integrity of the data from the photoplethysmography sensor.

7. The assessment generation system of claim 5 wherein the one or more processing circuits generate the average pulse shape by averaging a spline representation of each of the buffered plurality of pulses to generate an average spline representation.

8. The assessment generation system of claim 5 wherein the one or more processing circuits are further configured to generate the waveform representation by computing at least one of an integral of the average pulse shape and a derivative of the average pulse shape.

9. An assessment generation system configured to determine a blood pressure characteristic of a user using a device comprising a photoplethysmography sensor and a motion sensor, wherein the photoplethysmography sensor is proximal to at least some skin of the user, the system comprising a processing circuit configured to:
   screen data from the motion sensor to determine an integrity of data from the photoplethysmography sensor;
   process the data from the photoplethysmography sensor, at least some processed data having integrity, to generate an average pulse shape;
   compute at least one of an integral of the average pulse shape and a derivative of the average pulse shape; and
   determine the blood pressure characteristic using the average pulse shape and at least one of the integral and the derivative.

\* \* \* \* \*